US010710977B2

(12) United States Patent
Tanima et al.

(10) Patent No.: US 10,710,977 B2
(45) Date of Patent: Jul. 14, 2020

(54) METHOD FOR PRODUCING GEOMETRICAL ISOMER OF OXIMINO COMPOUND

(71) Applicant: Nissan Chemical Corporation, Chuo-ku (JP)

(72) Inventors: Daisuke Tanima, Funabashi (JP); Yoshiyuki Kusuoka, Funabashi (JP); Keisuke Tsuji, Funabashi (JP)

(73) Assignee: Nissan Chemical Corporation, Chuo-ku (JP)

( * ) Notice: Subject to any disclaimer, the term of this patent is extended or adjusted under 35 U.S.C. 154(b) by 0 days.

(21) Appl. No.: 16/484,337

(22) PCT Filed: Feb. 8, 2018

(86) PCT No.: PCT/JP2018/004391
§ 371 (c)(1),
(2) Date: Aug. 7, 2019

(87) PCT Pub. No.: WO2018/147368
PCT Pub. Date: Aug. 16, 2018

(65) Prior Publication Data
US 2019/0367479 A1    Dec. 5, 2019

(30) Foreign Application Priority Data

Feb. 8, 2017   (JP) ................. 2017-021298
Dec. 15, 2017  (JP) ................. 2017-241013

(51) Int. Cl.
*C07D 401/12*     (2006.01)

(52) U.S. Cl.
CPC ........ *C07D 401/12* (2013.01); *C07B 2200/09* (2013.01)

(58) Field of Classification Search
CPC .................................................. C07D 401/12
USPC ...................................................... 546/275.4
See application file for complete search history.

(56) References Cited

U.S. PATENT DOCUMENTS

| 4,158,015 | A | 6/1979 | Paul |
| 4,434,182 | A | 2/1984 | Cruickshank et al. |
| 5,130,486 | A | 7/1992 | Konyo et al. |
| 5,442,063 | A | 8/1995 | Takase et al. |
| 5,627,284 | A | 5/1997 | Takase et al. |
| 9,434,684 | B2 | 9/2016 | Iwasa et al. |
| 9,920,046 | B2 | 3/2018 | Iwasa et al. |
| 9,974,305 | B2 | 5/2018 | Kuwahara et al. |
| 10,029,986 | B2 | 7/2018 | Mita et al. |
| 10,231,454 | B2 | 3/2019 | Kuwahara et al. |
| 2011/0105794 | A1 | 5/2011 | Zierke et al. |
| 2019/0382372 | A1 | 12/2019 | Saito et al. |

FOREIGN PATENT DOCUMENTS

| EP | 0 435 687 A2 | 7/1991 |
| JP | 55-51049 A | 4/1980 |
| JP | 3-200754 A | 9/1991 |
| JP | 6-219986 A | 8/1994 |
| JP | 9-143138 A | 6/1997 |
| JP | 10-195064 A | 7/1998 |
| JP | 2016-11286 A | 1/2016 |
| JP | 2017-100972 A | 6/2017 |
| WO | WO 2011/093423 A1 | 8/2011 |
| WO | WO 2013/137075 A1 | 9/2013 |
| WO | WO 2014/010737 A1 | 1/2014 |
| WO | WO 2018/003924 A1 | 1/2018 |

OTHER PUBLICATIONS

U.S. Appl. No. 16/411,753, filed Jun. 14, 2019, US 2019-0382372 A1, Saito, H., et al.
U.S. Appl. No. 16/094,153, filed Oct. 16, 2018, US 2019-0133122 A1, Hasunima, et al.
International Search Report dated Apr. 10, 2018 in PCT/JP2018/004391 filed Feb. 8, 2018.
"Experimental Chemistry 14, Synthesis and Reactions of Organic Compounds III," The Chemical Society of Japan, Feb. 20, 1978, 4 Pages.
Office Action dated Dec. 27, 2019 in co-pending U.S. Appl. No. 16/441,753.

*Primary Examiner* — Taofiq A Solola
(74) *Attorney, Agent, or Firm* — Oblon, McClelland, Maier & Neustadt, L.L.P.

(57) ABSTRACT

Provided is a novel process for selectively producing the E-geometrical isomer or Z-geometrical isomer of an oximino compound useful as a medicine or agrochemical. In the process, a mixture of geometrical isomers of an oximino compound represented by formula (EZ)-1 is mixed with an acidic compound to produce the E-isomer of the oximo compound represented by the formula (E)-1 or the Z-isomer of the oximino compound represented by the formula (Z)-1 in high yields with high stereoselectivity.

11 Claims, 4 Drawing Sheets

METHOD FOR PRODUCING GEOMETRICAL ISOMER OF OXIMINO COMPOUND

TECHNICAL FIELD

The present invention relates to a process for producing a geometrical isomer of an oximino compound useful as a medicine and an agrochemical.

BACKGROUND ART

Some kinds of oximino compounds are known as agrochemically or medicinally useful compounds (Patent Documents 1 to 5). In general, oximino compounds have two geometrical isomers, isomers having an E-configuration (hereinafter referred to as E-isomers) and isomers having a Z-configuration [hereinafter referred to as Z-isomers], owing to the presence of an oximino group. It is possible to convert E-isomers to Z-isomers and vice versa or convert either isomers to a mixture of both isomers by known processes. For example, production of a Z-isomer from an E-isomer by light irradiation (Patent Documents 1 and 2), production of a Z-isomer from an E-isomer by treatment with an acidic compound (Patent Document 6), production of an E-isomer from a Z-isomer by treatment with an acidic compound (Patent Documents 4, 5, 7 and 8) and production of a mixture of an E-isomer and a Z-isomer from an E-isomer by light irradiation (Patent Document 3) are known.

PRIOR ART DOCUMENTS

Patent Documents

Patent Document 1: WO2014/010737
Patent Document 2: JP-A-2016-011286
Patent Document 3: WO2013/137075
Patent Document 4: JP-A-H06-219986
Patent Document 5: EP0435687A
Patent Document 6: JP-A-H10-195064
Patent Document 7: JP-A-H09-143138
Patent Document 8: WO2011/093423

DISCLOSURE OF INVENTION

Technical Problem

Oximino compounds are usually obtained as a mixture of the E-isomer and the Z-isomer. E-isomers and Z-isomers are so close structurally that it is very difficult to selectively remove the E- or Z-isomer from a mixture of them by usual purification operations such as column chromatography. When either isomer is used as a medicine or an agrochemical, the other geometrical isomer present in the product as an impurity can affect the quality and performance of the product.

Therefore, there is a demand for development of a novel process for producing a desired isomer of an oximino compound from an undesired isomer of the oximino compound.

Solution to Problem

As a result of extensive research to solve the above-mentioned problem, the present inventors have found that the E- or Z-isomer of an oximino compound can be produced selectively by isomerization treatment of a mixture of the E- and Z-isomers of the oximino compound represented by the formula (EZ)-1 with a controlled amount of an acidic compound, and have accomplished the present invention.

Namely, the present invention provides the following [1] to [11].

[1] A process for stereoselectively producing an oximino compound which produces the E-isomer of the oximino compound represented by the formula (E)-1;

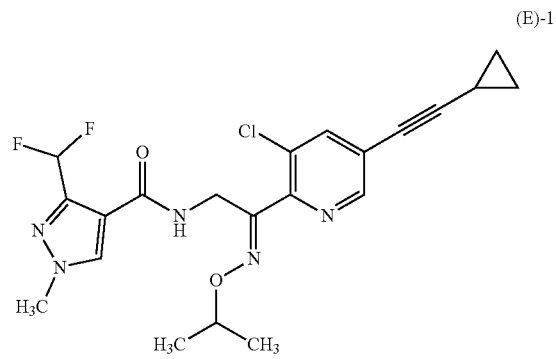 [SMILES: CC(C)O/N=C(\CNC(=O)c1cn(C)nc1C(F)F)c1ncc(C#CC2CC2)cc1Cl]

(E)-1 or the Z-isomer of the oximino compound represented by (Z)-1;

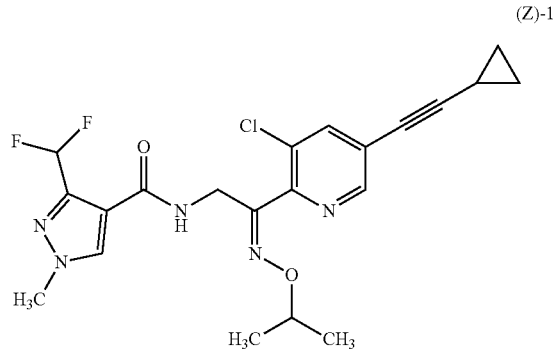 [SMILES: CC(C)O/N=C(/CNC(=O)c1cn(C)nc1C(F)F)c1ncc(C#CC2CC2)cc1Cl]

(Z)-1 from a mixture of geometrical isomers of the oximino compound represented by the formula (EZ)-1;

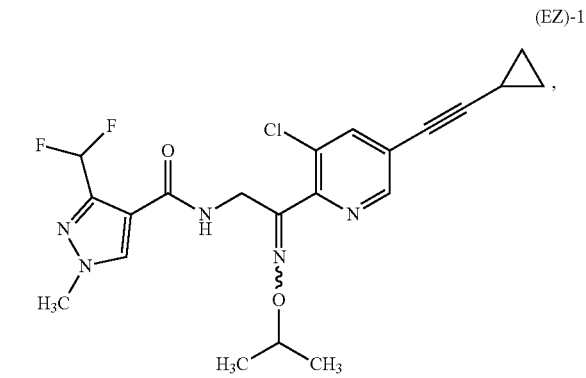 [SMILES: CC(C)ON=C(CNC(=O)c1cn(C)nc1C(F)F)c1ncc(C#CC2CC2)cc1Cl]

(EZ)-1 produces the Z-isomer of the oximino compound represented by the formula (Z)-1 from the E-isomer of the oximino compound represented by the formula (E)-1, or produces the E-isomer of the oximino compound represented by the formula (E)-1 from the Z-isomer of the oximino compound represented by the formula (Z)-1, which comprises:
(i) mixing a mixture of the geometrical isomers represented by the formula (EZ)-1 or the Z-isomer of the oximino compound represented by the formula (Z)-1 as a starting material with at most 0.1 equivalent of an acidic compound, relative to the starting material, in a solvent to produce the E-isomer of the oximino compound represented by the formula (E)-1, or
(ii) mixing a mixture of the geometrical isomers represented by the formula (EZ)-1 or the E-isomer of the oximino compound represented by the formula (E)-1 as a starting material with at least 0.7 equivalent of an acidic compound, relative to the starting material, in a solvent to produce the Z-isomer of the oximino compound represented by the formula (Z)-1.
[2] The process for stereoselectively producing an oximino compound according to [1], wherein the starting material is a mixture of the geometrical isomers represented by the formula (EZ)-1.
[3] The process for stereoselectively producing an oximino compound according to [1] or [2], wherein the acidic compound is added after the starting material is dissolved in the solvent.
[4] The process for stereoselectively producing an oximino compound according to any one of [1] to [3], which produces the E-isomer of the oximino compound represented by the formula (E)-1 by using at least 0.01 equivalent and at most 0.07 equivalent of the acidic compound, relative to the starting material.
[5] The process for stereoselectively producing an oximino compound according to any one of [1] to [3], which produces the Z-isomer of the oximino compound represented by the formula (Z)-1 by using at least 1.0 equivalent and at most 2.0 equivalent of the acidic compound, relative to the starting material.
[6] The process for stereoselectively producing an oximino compound according to any one of [1] to [5], wherein the acidic compound is a hydrogen halide, sulfuric acid or methanesulfonic acid.
[7] The process for stereoselectively producing an oximino compound according to any one of [1] to [6], wherein as the solvent, one or more solvents selected from the group consisting of aromatic hydrocarbon solvents, ether solvents, ketone solvents, ester solvents and halohydrocarbon solvents is used.
[8] The process for stereoselectively producing an oximino compound according to [7], wherein as the solvent, one or more solvents selected from the group consisting of toluene, orthoxylene, cyclopentyl methyl ether, tertiary butyl methyl ether, dimethoxyethane, diethylene glycol dimethyl ether, methyl ethyl ketone, ethyl acetate and 1,2-dichloroethane is used.
[9] The process for stereoselectively producing an oximino compound according to any one of [1] to [8], which further comprises, after mixing the starting material and the acidic compound in the solvent, a step of adding one or more solvents selected from aliphatic hydrocarbon solvents.
[10] The process for stereoselectively producing an oximino compound according to [9], wherein the aliphatic hydrocarbon solvent is normal heptane.
[11] The process for stereoselectively producing an oximino compound according to any one of [1] to [10], wherein crystals, a salt or a solvate of the salt or a solvate is separated from the reaction system.

Advantageous Effects of Invention

The present invention provides an industrially useful production process for producing an oximino compound useful as a medicine or agrochemical in high yields with high stereoselectivity.

DESCRIPTION OF EMBODIMENTS

Figure 1:
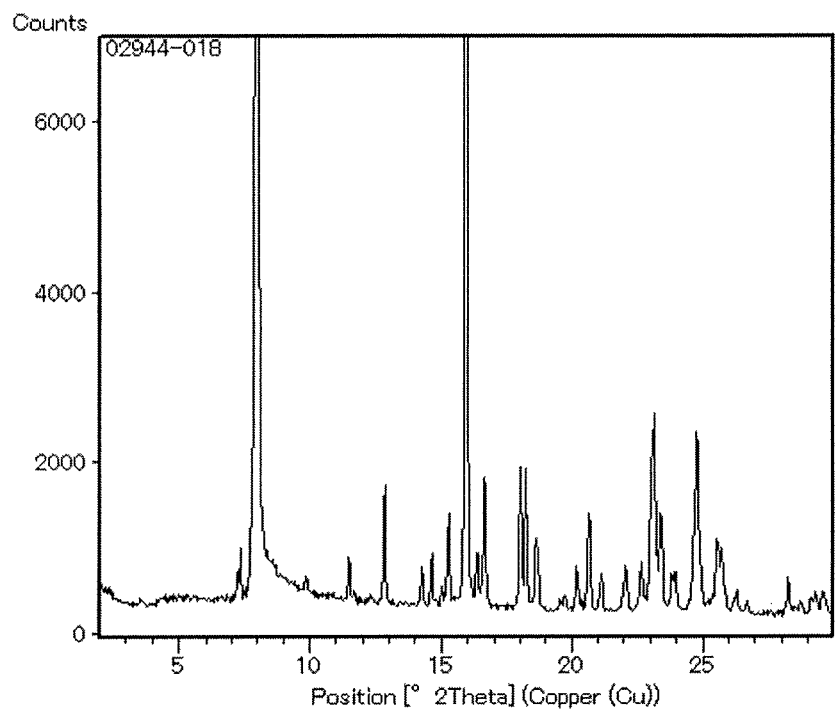
FIG. 1 A powder X-ray diffraction chart of (E)-N-[2-[3-chloro-5-(cyclopropylethynyl)pyridin-2-yl]-2-(isopropoximino)ethyl]-3-(difluoromethyl)-1-methyl-1H-pyrazole-4-carboxamide obtained in Example 1-1.

Now, the present invention will be described in detail.
The oximino compound covered by the present invention has two isomers having different configurations owing to the presence of an oximino group. Herein, among the two isomers, the isomer having an E-configured oximino group is called the E-isomer, and the isomer having a Z-configured oximino group is called the Z-isomer.
The E-isomer in the present invention covers a geometrical mixture having an E-isomer/Z-isomer mixing ratio of from 90/10 to 100/0, and the Z-isomer in the present invention covers a geometrical mixture having an E-isomer/Z-isomer mixing ratio of from 10/90 to 0/100, and the mixture of the E-isomer and the Z-isomer in the present invention covers a geometrical mixture having an E-isomer/Z-isomer mixing ratio of more than 10/90 and less than 90/10. The E-isomer/Z-isomer mixing ratio can be calculated from the results of qualitative analysis by any measuring techniques such as high-performance liquid chromatography, gas chromatography and nuclear magnetic resonance spectrometry.

Herein, formulae having an oximino group containing a bond represented by a wavy line [such as the formula (EZ)-1] represent a mixture of the E-isomer and the Z-isomer.

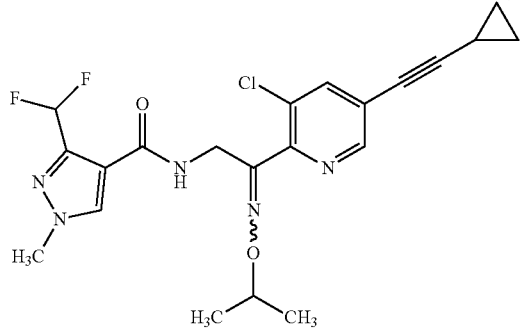

(EZ)-1

Herein, n- denotes normal, i- denotes iso, s- denotes secondary, and tert- or t- denotes tertiary, respectively, and o- denotes ortho, m- denotes metha, and p- denotes para.

Herein, as a basic compound, an inorganic base, an organic base or the like may be mentioned.

As an inorganic base, for example, lithium hydroxide, sodium hydroxide, potassium hydroxide, cesium hydroxide, magnesium hydroxide, calcium hydroxide, barium hydroxide, lithium carbonate, sodium carbonate, potassium carbonate, cesium carbonate, sodium hydrogen carbonate, potassium hydrogen carbonate, cesium hydrogen carbonate, ammonium hydrogen carbonate, sodium acetate, potassium acetate, cesium acetate, calcium acetate, barium acetate, sodium phosphate, potassium phosphate, sodium hydrogen phosphate, potassium hydrogen phosphate or the like may be mentioned.

As an organic base, for example, ammonia, ethylamine, diethylamine, triethylamine, diisopropylethylamine, tributylamine, pyridine, 2-methylpyridine, 3-methylpyridine, 4-methylpyridine, 2,3-lutidine, 2,4-lutidine, 2,6-lutidine, 3,5-lutidine, diazabicycloundecene, 1,4-diazabicyclo[2.2.2]octane, 1,1,3,3-tetramethylguanidine or the like may be mentioned.

Next, the process of the present invention for producing the compound represented by the formula (E)-1 [hereinafter referred to as Compound (E)-1] from the compound represented by the formula (EZ)-1 [hereinafter referred to as Mixture (EZ)-1], the process of the present invention for producing the compound represented by the formula (Z)-1 [hereinafter referred to as Compound (Z)-1] from Mixture (EZ)-1, the process of the present invention for producing Compound (E)-1 from Compound (Z)-1, and the process of the present invention for producing Compound (Z)-1 from Compound (E)-1 will be described in detail.

[Process 1]

Reaction Scheme 1

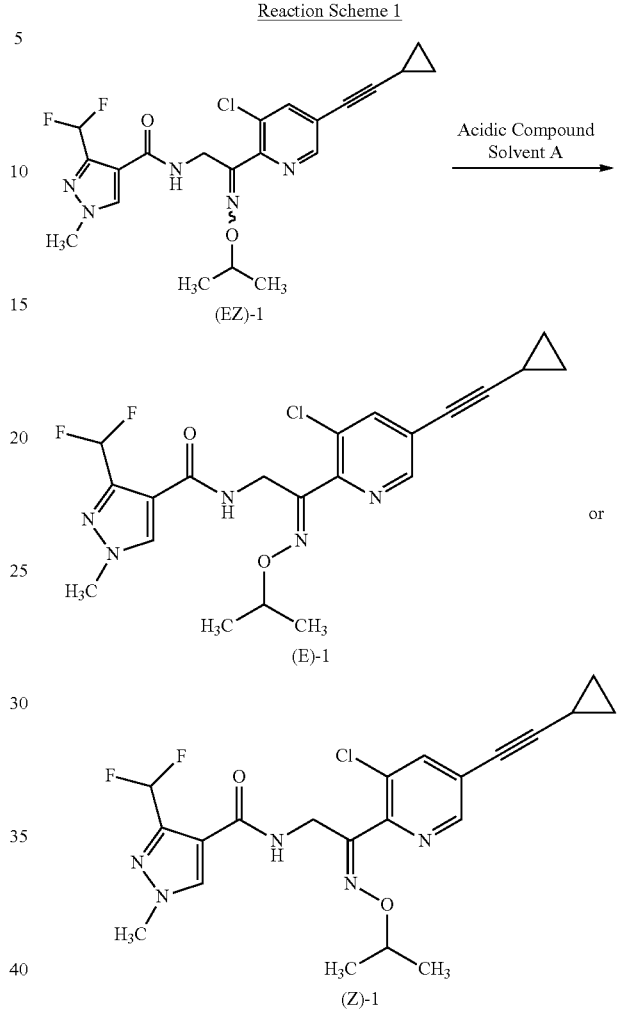

Mixture (EZ)-1 and an acidic compound are mixed in a solvent (hereinafter referred to as Solvent A) and reacted, and then the desired product is precipitated as crystals. In this case, by using a controlled amount of the acidic compound, it is possible to selectively produce either of the geometrical isomers Compound (E)-1 and Compound (Z)-1. Similarly, by using a controlled amount of the acidic compound, it is possible to selectively produce Compound (E)-1 from Compound (Z)-1, or selectively produce Compound (Z)-1 from Compound (E)-1.

For production of Compound (E)-1, the acidic compound may be used in an amount of from 0.00001 to 0.1 equivalent, preferably from 0.001 to 0.1 equivalent, more preferably from 0.01 to 0.07 equivalent, relative to the starting material [Mixture (EZ)-1 or Compound (Z)-1].

For production of Compound (Z)-1, the acidic compound may be used in an amount of from 0.7 to 10 equivalents, preferably from 0.7 to 5 equivalents, more preferably from 0.7 to 2 equivalents, relative to the starting material [Mixture (EZ)-1 or Compound (E)-1].

As the acidic compound, for example, a hydrogen halide, an inorganic acid, a carboxylic acid, a sulfonic acid or the like may be mentioned.

As the hydrogen halide, for example, hydrogen fluoride, hydrogen chloride, hydrogen bromide, hydrogen iodide or the like may be mentioned.

As the inorganic acid, for example, nitric acid, sulfuric acid, phosphoric acid, chloric acid, boric acid, perchloric acid or the like maybe mentioned.

As the carboxylic acid, for example, formic acid, acetic acid, trifluoroacetic acid, trichloroacetic acid, propionic acid, butyric acid, valeric acid, pivalic acid, isovaleric acid, caproic acid, enathic acid, caprylic acid, pelargonic acid, caprylic acid, lauric acid, myristic acid, palmitic acid, stearic acid, acrylic acid, methacrylic acid, tiglic acid, oleic acid, linolenic acid, linoleic acid, arachidonic acid, oxalic acid, malonic acid, succinic acid, glutaric acid, adipic acid, fumaric acid, maleic acid, malic acid, lactic acid, ascorbic acid, citric acid, mandelic acid, tartaric acid, pyruvic acid, benzoic acid, o-methylbenzoic acid, m-methylbenzoic acid, p-methylbenzoic acid, o-trifluoromethylbenzoic acid, m-trifluoromethylbenzoic acid, p-trifluoromethylbenzoic acid, o-chlorobenzoic acid, m-chlorobenzoic acid, p-chlorobenzoic acid, o-nitrobenzoic acid, m-nitrobenzoic acid, p-nitrobenzoic acid, phthalic acid, isophthalic acid, terephthalic acid, salicylic acid, gallic acid, mellitic acid, cinnamic acid or the like may be mentioned.

As the sulfonic acid, for example, methanesulfonic acid, ethanesulfonic acid, 10-camphorsulfonic acid, trifluoromethanesulfonic acid, benzenesulfonic acid, o-toluenesulfonic acid, m-toluenesulfonic acid, p-toluenesulfonic acid, o-trifluoromethylbenzenesulfonic acid, m-trifluoromethylbenzenesulfonic acid, p-trifluoromethylbenzenesulfonic acid, o-chlorobenzenesulfonic acid, m-chlorobenzenesulfonic acid, p-chlorobenzenesulfonic acid, o-nitrobenzenesulfonic acid, m-nitrobenzenesulfonic acid, p-nitrobenzenesulfonic acid or the like may be mentioned.

The acidic compound is preferably a hydrogen halide, sulfuric acid or methanesulfonic acid, more preferably hydrogen chloride, hydrogen bromide or sulfuric acid.

These acidic compounds may contain water. These acidic compounds may be used as a mixture of at least two.

Mixture (EZ)-1 used in the present invention can be synthesized by known methods described, for example, in JP-A-2016-011286 and has a mixing ratio of the E-isomer and the Z-isomer within the above-mentioned range.

As the solvent used as Solvent A, an aromatic hydrocarbon solvent, a halohydrocarbon solvent, an alcohol solvent, an ether solvent, an ester solvent, an amide solvent, a nitrile solvent, a ketone solvent, dimethyl sulfoxide or the like may be mentioned.

As the aromatic hydrocarbon solvent, for example, benzene, toluene, o-xylene, m-xylene, p-xylene, chlorobenzene, 1,2-dichlorobenzene, 1,3-dichlorobenzene, 1,4-dichlorobenzene, and nitrobenzene or the like may be mentioned. As the halohydrocarbon solvent, for example, chloroform, dichloromethane, dichloroethane or the like may be mentioned. As the alcohol solvent, for example, methanol, ethanol, 1-propanol, 2-propanol, 1-butanol, 2-butanol, t-butyl alcohol or the like may be mentioned. As the ether solvent, diethyl ether, tetrahydrofuran, cyclopentyl methyl ether, tertiary butyl methyl ether, 1,4-dioxane, dimethoxyethane, diethylene glycol dimethyl ether or the like may be mentioned. As the ester solvent, for example, methyl acetate, ethyl acetate, butyl acetate, methyl propionate, or the like may be mentioned. As the amide solvent, for example, N,N-dimethylformamide, N,N-dimethylacetamide, N-methylpyrrolidone or the like may be mentioned. As the nitrile solvent, for example, acetonitrile, propionitrile or the like may be mentioned. As the ketone solvent, for example, methyl ethyl ketone, methyl isobutyl ketone or the like may be mentioned.

Solvent A is preferably an aromatic hydrocarbon solvent, a halohydrocarbon solvent, an ether solvent, an ester solvent, a ketone solvent or the like, more preferably toluene, o-xylene, 1,2-dichloroethane, cyclopentyl methyl ether, t-butyl methyl ether, dimethoxyethane, diethylene glycol dimethyl ether, ethyl acetate or methyl ethyl ketone, further preferably 1,2-dichloroethane or ethyl acetate.

These solvents may be used alone or as a mixture of at least two.

The amount of the solvent (in the case of a mixture of two or more solvents, the total amount thereof) is from 0.01 to 100 parts by mass, preferably from 0.1 to 50 parts by mass, more preferably from 0.5 to 20 parts by mass, further preferably from 1 to 10 parts by mass, relative to the starting material.

The reaction temperature for the reaction of the mixture of the starting material and the acidic compound in the solvent is usually from −20 to 150° C., preferably from 0 to 100° C., more preferably from 10 to 60° C. The crystallization temperature is usually from −20 to 150° C., preferably −10 to 80° C., more preferably from 10 to 50° C.

The reaction time for the reaction of the mixture of the starting material and the acidic compound in the solvent is usually from 1 minute to 1,000 hours, preferably from 5 minutes to 100 hours, more preferably from 10 minutes to 48 hours. The crystallization time is usually from 1 minute to 1,000 hours, preferably from 5 minutes to 500 hours, more preferably from 10 minutes to 100 hours, though it depends on the concentrations of the reactants and the reaction temperature.

The desired product may be recovered by separating precipitated crystals from the reaction system by filtration, although there is no particular restriction on the treatment after the reaction. The oximino compound remaining in the filtrate may be used as the starting material for another run of the process of the present invention, if necessary, after concentration of the filtrate. If necessary, the crystals recovered may be purified by any purification technique such as recrystallization, to give the desired product with a higher purity.

The reaction sometimes gives the desired product in the form of a salt with the acidic compound used in the reaction. In such a case, even though the salt can be recovered in the same manner as described above, the salt may be neutralized with a basic compound such as sodium hydroxide or aqueous sodium hydroxide, if necessary after successive addition of water and an organic solvent, and if necessary, after dissolved in the organic solvent. After neutralization, the desired product can be obtained by ordinary post-treatment such as liquid-liquid separation, if necessary after addition of water, if necessary followed by concentration.

The reaction sometimes gives the desired product in an associated form containing the solvent used in the reaction (hereinafter referred to as a solvate) as a result of solvation with the solvent. In such a case, even though the solvate can be recovered in the same manner as described above, if necessary, the solvate obtained may be dissolved or suspended in a solvent which does not form a solvate with the desired product and then subjected to liquid-liquid separation, if necessary after addition of water, and if necessary to ordinary post-treatment such as concentration to give the desired product.

The reaction sometimes gives the desired product in the form of a solvated salt containing the acidic compound and the solvent used in the reaction. In such a case, the solvated salt can be recovered in the same manner as described above, if necessary, it may be subjected to a combination of some of the above-mentioned post-treatments to give the desired product.

[Process 2]

Solvent B is preferably added dropwise at a rate of from 0.001 part by mass to 100 parts by mass per hour, preferably at a rate of from 0.01 part by mass to 10 parts by mass per hour, more preferably at a rate of from 0.1 part by mass to 3 parts by mass per hour, relative to the starting material.

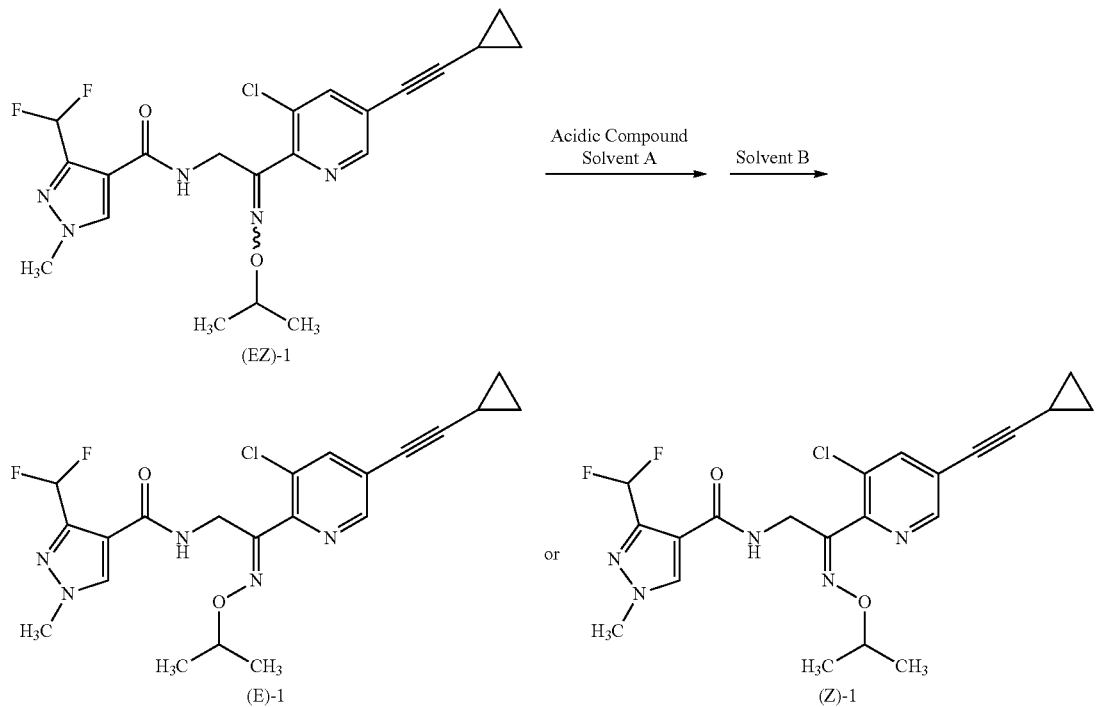

Reaction Scheme 2

Mixture (EZ)-1 is reacted in the presence of an acidic compound in a solvent (hereinafter referred to as Solvent A), and then another solvent (hereinafter referred to as Solvent B) is added to obtain the desired product as crystals. In this case, by using a controlled amount of the acidic compound, it is possible to selectively produce either of the geometrical isomers Compound (E)-1 and Compound (Z)-1. Similarly, by using a controlled amount of the acidic compound, it is possible to selectively produce Compound (E)-1 from Compound (Z)-1, or selectively produce Compound (Z)-1 from Compound (E)-1.

The acidic compound and its amount are the same as described for Process 1.

As the solvent used as Solvent A, those mentioned for Process 1 may, for example, be mentioned. These solvents may be alone or as a mixture of at least two. The amount of the solvent is the same as described for Process 1.

As the solvent used as Solvent B, an aliphatic hydrocarbon solvent such as n-pentane, n-hexane, cyclohexane, n-heptane, n-octane and i-octane may be mentioned. Preferred are n-pentane, n-hexane and n-heptane, and more preferred is n-heptane. These solvents may be used alone or as a mixture of at least two.

The amount of Solvent B (in the case of a mixture of two or more solvents, the total amount thereof) is from 0.01 to 1,000 parts by mass, preferably from 0.1 to 100 parts by mass, more preferably from 0.5 to 30 parts by mass, and still more preferably from 1 to 10 parts by mass, relative to the starting material.

Although there is no particular restriction on the treatment after the reaction, the treatment described for Process 1 affords the desired product with a higher purity.

The reaction sometimes gives the desired product as a salt with the acidic compound used in the reaction, a solvate with the solvent used in the reaction or a solvated salt containing the acidic compound and the solvent used in the reaction. The desired product can be obtained by the post-treatment described for Process 1, if necessary.

By using the process of the present invention, it is possible to provide a process useful for industrial production of an oximino compound. Although from the standpoint of industrial production, high yields and high stereoselectivity are important, reduction of by-products and the reaction time and production of the desired product with simple operations such as filtration are also important.

EXAMPLES

Now, the present invention will be explained in more detail by describing specific synthetic examples as working examples of the present invention, but the present invention is by no means restricted thereto.

$^1$H-NMR in the Examples and Reference Examples represents proton nuclear magnetic resonance spectrum. Similarly, HPLC represents high-performance liquid chromatography, LC/MS represents a liquid chromatography-mass spectrometer, IC represents ion chromatography, and Rt represents retention time.

¹H-NMR was measured by using tetramethylsilane as the standard in a deuterated dimethyl sulfide solvent at 300 MHz. The symbols in the ¹H-NMR data presented later have the following meanings.

s: singlet, d: doublet, t: triplet, sep: septet, m: multiplet.

[Qualitative Analysis]

Qualitative analysis by HPLC was performed under the following measuring conditions.
Column: Inertsil ODS-SP 250 mm 4.6 mm φ 5 μm (GL Sciences Inc.)
Flow Rate: 1.0 mL/min
Column Temperature: 40° C.
Detection Wavelength: UV 254 nm
Eluent: acetonitrile/water/trifluoroacetic acid=600/400/1 (volume ratio)
Solvent for Sample Solution: acetonitrile/triethylamine=98/2 (volume ratio)

[Quantitative Analysis]

Quantitative analysis by HPLC was performed by an internal standard method using 4-methylbiphenyl as an internal standard under the same measuring conditions as the qualitative analysis. The analytical samples were adjusted to basicity with 2.0 vol % triethylamine/acetonitrile.

The content of the desired Z- or E-isomer in crystals produced was calculated by the results of the above-mentioned quantitative analysis, and the content of the other isomer is calculated from the content of the desired isomer and the peak area ratio in the HPLC results, taking the UV sensitivity of the Z- and E-isomers (Z-isomer/E-isomer=1.097) into consideration, unless otherwise noted. The "quantitative yields" in the Examples were calculated from the sum of the contents of the Z-isomer and the E-isomer, and the "Z-isomer/E-isomer ratios" were calculated from the contents of the Z-isomer and the E-isomer.

[Mass Spectrometric Analysis]

Mass spectrometric analysis with a LC/MS was carried out under the following conditions.
Column: Sun Fire C18 50 mm 2.1 mm φ 2.5 μm (WATERS)
Flow Rate: 0.3 mL/min
Column Temperature: 40° C.
Detection Wavelength: UV 254 nm
Eluent:

TABLE 1

| Time (min) | A:B (Volume Ratio) |
|---|---|
| 0 | 90:10 |
| 0 to 5 | Gradient from 90:10 to 5:95 |
| 5 to 8 | 5:95 |

A: 0.1 vol % Aqueous formic acid
B: Acetonitrile

[X-Ray Diffraction]

Powder X-ray diffraction of crystals was measured under the following conditions. Instrument: X'pert Pro MPD (PANalytical Ltd.)
X ray Source: Cu
Voltage: 45 kV
Current: 40 mA
Data range: 2.0191 to 39.7471° 2 Th.
Scanning Axis: Gonio
Step size: 0.0260° 2 Th.
Scan step time: 47.9400 sec
Scan mode: Continuous
PSD mode: Scanning
PSD distance: 3.35° 2 Th.
Divergence slit type: Automatic
Radiation width: 10.00 mm
Sample width: 10.00 mm
Measured temperature: 25.00° C.
K-Alpha1: 1.54060 A
K-Alpha2: 1.54443 A
K-Beta: 1.39225 A
K-A2/K-A1 ratio: 0.50000
Goniometer radius: 240.00 mm
Focus-DS distance: 100.00 mm The expression "parts by mass" in the Examples is relative to the starting material, unless otherwise noted, and the expression "equivalent" is relative to the starting material, unless otherwise noted.

"4.5 mass % hydrogen chloride/ethyl acetate" in the Examples is an ethyl acetate solution containing 4.5 mass % of hydrogen chloride, manufactured by Fuji Pure Chemicals co., ltd. or Tokyo Chemical Industry Co., Ltd. Similarly, "4.4 mass % hydrogen chloride/ethyl acetate" is an ethyl acetate solution containing 4.4 mass % of hydrogen chloride (manufactured by Fuji Pure Chemicals co., ltd.), and "15.5 mass % hydrogen chloride/cyclopentyl methyl ether" or "15.5 mass % hydrogen chloride/CPME" is a cyclopentyl methyl ether solution containing 15.5 mass % of hydrogen chloride (manufactured by WATANABE CHEMICAL INDUSTRIES, LTD.).

Example 1

Process 2 described earlier was carried out by using various equivalents of hydrogen chloride as the acidic compound.

Example 1-1

Preparation of (E)-N-[2-[3-chloro-5-(cyclopropylethynyl)pyridin-2-yl]-2-(isopropoximino)ethyl]-3-(difluoromethyl)-1-methyl-1H-pyrazole-4-carboxamide [Hereinafter Referred to as Compound (E)-1]

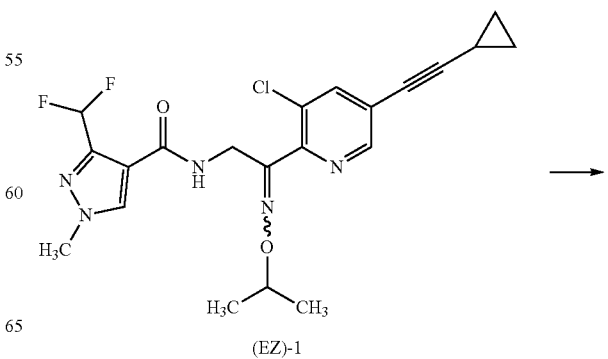

(EZ)-1

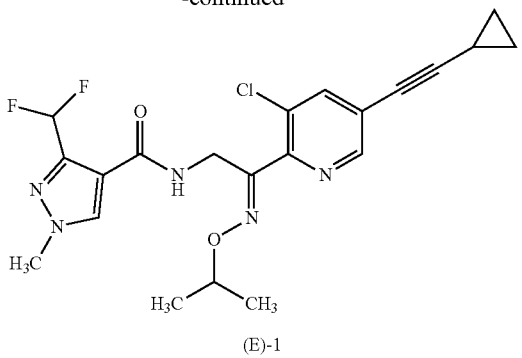

(E)-1

5.40 g of (EZ)—N-[2-[3-chloro-5-(cyclopropylethynyl)pyridin-2-yl]-2-(isopropoximino)ethyl]-3-(difluoromethyl)-1-methyl-1H-pyrazole-4-carboxamide [hereinafter referred to as Compound (EZ)-1] (Z-isomer/E-isomer=51.7/48.3), 5.40 g, or 1 part by mass relative to the starting material, of 1,2-dichloroethane, 0.243 g of 4.5 mass % hydrogen chloride/ethyl acetate (containing 0.025 equivalent of hydrogen chloride), and 13.7 g of ethyl acetate to make a total of 2.5 parts by mass relative to the starting material of ethyl acetate, were mixed at 25° C. The mixed solution was stirred at the same temperature for 30 minutes. 27.0 g of n-heptane was added dropwise to the resulting reaction solution over 10 hours, whereupon crystals precipitated. The resulting suspension was stirred at 25° C. for 8 hours, then cooled to 5° C. and stirred at the same temperature for 3 hours. The crystals were recovered by filtration and washed with a liquid mixture of 10.8 g of n-heptane and 2.7 g of ethyl acetate to give 4.02 g of the desired product as pale yellow crystals [the quantitative yield of Compound (E)-1 was 74.5%]. According to qualitative analysis of the resulting crystals by HPLC, the area ratio of the peak for the Z-isomer to that for the E-isomer was 0.6/99.4 (Rt=10.8 minutes/12.1 minutes), and the total area percentage of the two peaks was 99.6%. m.p.: 113 to 114° C.

The ¹H-NMR data for Compound (E)-1 obtained in Example 1-1 are shown below.

¹H-NMR: δ8.42 (d, J=1.8 Hz, 1H), 8.30 (t, J=5.7 Hz, 1H), 8.03 (s, 1H), 7.91 (d, J=1.8 Hz, 1H), 7.10 (t, J=54.3 Hz, 1H), 4.42 (d, J=5.7 Hz, 2H), 4.35 (sep, J=6.6 Hz, 1H), 3.83 (s, 3H), 1.60-1.50 (m, 1H), 1.23 (d, J=6.6 Hz, 6H), 0.95-0.85 (m, 2H), 0.80-0.73 (m, 2H).

Example 1-2

Preparation of 1,2-dichloroethane Hemisolvate of (Z)—N-[2-[3-chloro-5-(cyclopropylethynyl)pyridin-2-yl]-2-(isopropoximino)ethyl]-3-(difluoromethyl)-1-methyl-1H-pyrazole-4-carboxamide Hydrochloride [Hereinafter Referred to as Compound (Z)-2]

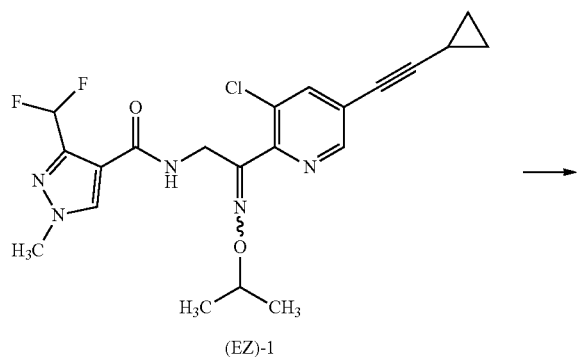

(EZ)-1

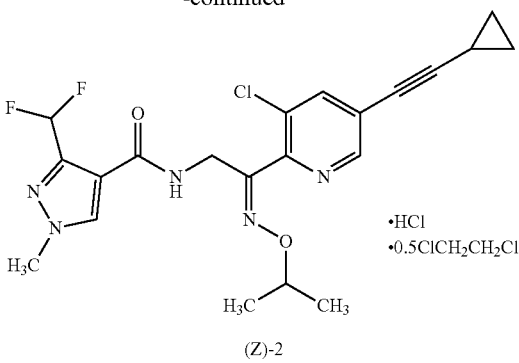

(Z)-2

5.40 of g Compound (EZ)-1 (Z-isomer/E-isomer=51.7/48.3), 5.40 g, or 1 part by mass relative to the starting material, of 1,2-dichloroethane and 14.6 g of 4.5 mass % hydrogen chloride/ethyl acetate (containing 1.5 equivalents of hydrogen chloride and 2.5 parts by mass of ethyl acetate relative to the starting material) were mixed at 25° C. The mixed solution was stirred at the same temperature for 4 hours, whereupon crystals precipitated. 27.0 g of n-heptane was added dropwise to the resulting suspension over 10 hours, and the suspension was stirred at 25° C. for 8 hours. The suspension was cooled to 5° C. and stirred at the same temperature for 3 hours. The precipitated crystals were recovered by filtration and washed with a liquid mixture of 10.8 g of n-heptane and 2.70 g of ethyl acetate to give 6.12 g of the desired product as pale yellow crystals [the quantitative yield of Compound (Z)-1 was 95.3%]. According to qualitative analysis of the resulting crystals by HPLC, the area ratio of the peak for the Z-isomer to that for the E-isomer was 98.0/2.0 (Rt=10.8 minutes/12.1 minutes), and the total area percentage of the two peaks was 99.2%. X-ray single-crystal structural analysis under the following conditions identified the crystals as Compound (Z)-2 having a Z-configured oximino group.

The ¹H-NMR data for Compound (Z)-2 are shown below.

¹H-NMR: δ8.52 (t, J=6.0 Hz, 1H), 8.44 (d, J=1.8 Hz, 1H), 8.14 (s, 1H), 7.88 (d, J=1.8 Hz, 1H), 7.11 (t, J=54.3 Hz, 1H), 4.35-4.05 (m, 6H), 3.85 (s, 2H, 0.5 molecule of 1,2-dichloroethane), 1.60-1.50 (m, 1H), 1.05 (d, J=6.3 Hz, 6H), 0.95-0.85 (m, 2H), 0.75-0.70 (m, 2H).

[Analysis Conditions]
Instrument: SMART APEXII ULTRA (Bruker AXS K.K.)
X-ray: CuKα (50 kV, 50 mA)
Measuring temperature: −50° C.

Examples 1-3 to 1-9

The reaction was carried out in accordance with Examples 1-1 and 1-2 by using various amounts of 4.5 mass % hydrogen chloride/ethyl acetate and adjusting the amount of ethyl acetate to 2.5 parts by mass relative to the starting material.

The amounts of hydrogen chloride in equivalents (represented as "HCl equivalents" in Table 2), the quantitative yield of Compound (Z)-1 or Compound (E)-1 contained in the crystals (represented as "quantitative yield" in Table 2), the overall purity of Compound (Z)-1 and Compound (E)-1 according to qualitative analysis by HPLC (represented as "purity" in Table 2) and the ratio of the Z-isomer and E-isomer calculated from the results of qualitative analysis by HPLC (represented as "Z/E ratio" in Table 2) are shown below in Table 2.

TABLE 2

| Ex. | HCl equivalents (eq) | Quantitative yield (%) | purity (%) | Z/E ratio |
|---|---|---|---|---|
| 1-1 | 0.025 | 74.5 | 99.6 | 0.6/99.4 |
| 1-3 | 0.05 | 78.0 | 99.6 | 5.7/94.3 |
| 1-4 | 0.10 | 76.8 | 99.7 | 12.1/87.9 |
| 1-5 | 0.25 | 77.6 | 99.3 | 31.3/68.7 |
| 1-6 | 0.50 | 77.4 | 99.1 | 66.3/33.7 |
| 1-7 | 0.75 | 71.8 | 99.4 | 97.7/2.3 |
| 1-8 | 1.00 | 93.2 | 98.9 | 98.2/1.8 |
| 1-9 | 1.25 | 95.2 | 99.2 | 98.2/1.8 |
| 1-2 | 1.50 | 95.3 | 99.1 | 98.0/2.0 |

Example 2

Process 1 described earlier was carried out by using various kinds of solvent and various kinds and equivalents of acidic compound.

Example 2-1

Preparation of Compound (E)-1 Using Cyclopentyl Methyl Ether as the Solvent and Methanesulfonic Acid as the Acidic Compound 2.0 g of Compound (EZ)-1 (Z-isomer/E-isomer=50.4/49.6) and 3 parts by mass of cyclopentyl methyl ether (hereinafter referred to as CPME) were mixed at 40° C. To the resulting mixed solution, 0.02 equivalent (85 mg) of methanesulfonic acid was added, and the mixed solution was stirred at 20° C. for 60 hours to precipitate crystals. After the precipitation of crystals, the suspension was cooled to 5° C. and stirred for 5 hours. The precipitated crystals were recovered by filtration and washed with 1 part by mass of the same solvent as used for the reaction, CPME, to give pale yellow crystals. According to quantitative analysis, the quantitative yield of Compound (E)-1 was 73.1%, and the ratio of the Z-isomer to the E-isomer was Z/E=0.4/99.6. According to qualitative analysis, the total area percentage of the peaks for the Z-isomer and the E-isomer was 99.9%.

Example 2-6

Preparation of the Sulfate of Compound (Z)-1 Using Cyclopentyl Methyl Ether as the Solvent and Sulfuric Acid as the Acidic Compound 2.0 g of Compound (EZ)-1 (Z-isomer/E-isomer=48.8/51.2) and 4 parts by mass of CPME were mixed at 40° C. 0.5 equivalent (218 mg) of concentrated sulfuric acid was added to the resulting mixed solution, and the mixed solution was stirred at the same temperature for 1.5 hours to precipitate crystals. After the precipitation of crystals, 0.6 equivalent (264 mg) of concentrated sulfuric acid was added to the suspension, and the suspension was stirred further for 20 hours, then cooled to 5° C. and stirred for 3 hours. The precipitated crystals were recovered by filtration and washed with the same solvent as used for the reaction, CPME (2 mL), to give the sulfate of Compound (Z)-1 as pale yellow crystals. According to quantitative analysis, the quantitative yield of Compound (E)-1 was 87.9%, and the ratio of the Z-isomer to the E-isomer was Z/E=94.6/5.4. According to qualitative analysis, the total area percentage of the peaks for the Z-isomer and the E-isomer was 98.8%.

Example 2-7

Preparation of Sulfate of Compound (Z)-1 Using Toluene as the Solvent and Sulfuric Acid as the Acidic Compound 1.5 g of Compound (EZ)-1 (Z-isomer/E-isomer=48.8/51.2) and 4 parts by mass of toluene were mixed at 30° C. 0.55 equivalent (240 mg) of 75 mass % aqueous sulfuric acid was added to the mixed solution, and the mixed solution was stirred at the same temperature for 2 hours to precipitate crystals. After the precipitation of crystals, 0.55 equivalent (240 mg) of 75 mass % aqueous sulfuric acid was added to the suspension at the same temperature, and the suspension was stirred further for 16 hours. The suspension was cooled to 0° C. and stirred for 3 hours. The precipitated crystals were recovered by filtration and washed with 2 parts by mass of the same solvent as used for the reaction, toluene, to give the sulfate of Compound (Z)-1 as pale yellow crystals. According to quantitative analysis, the quantitative yield of Compound (Z)-1 was 80.4%, and the ratio of the Z-isomer to the E-isomer was Z/E=95.1/4.9. According to qualitative analysis, the total area percentage of the peaks for the Z-isomer and the E-isomer was 97.9%.

Examples 2-2 to 2-5

The reaction was carried out in accordance with Example 2-1 by using various kinds of solvent and acidic compound. The reaction conditions and the results are shown in Table 3. The Table lists the kinds of solvent used in the column titled "solvent" with the amounts of the solvents in parts by mass in parentheses, and the kinds of acidic compound used in the column titled "acidic compound" with the amounts of the acidic compounds in equivalents in parentheses.

TABLE 3

| Ex. | Solvent (parts by mass) | Mixing temperature (° C.) | Acidic compound (eq.) | Stirring temperature (° C.) | Time (hr) | Filtration temperature (° C.) | Quantitative yield (%) | Z/E ratio | Purity (%) |
|---|---|---|---|---|---|---|---|---|---|
| 2-1 | CPME (3) | 40 | Methanesulfonic acid (0.02) | 20 | 60 | 5 | 73.1 | 0.4/99.6 | 99.9 |
| 2-2 | CPME (2) | 50 | 15.5 mass % hydrogen chloride/CPME (0.05) | 25 | 24 | 15 | 75.0 | 1.5/98.5 | 99.3 |
| 2-3 | CPME (3) | 40 | Concentrated sulfuric acid (0.02) | 20 | 60 | 5 | 71.1 | 2.7/97.3 | 99.9 |
| 2-4 | Toluene (2) | 50 | 75 mass % aqueous sulfuric acid (0.03) | 20 | 62 | 5 | 81.4 | 4.0/96.0 | 99.9 |

TABLE 3-continued

| Ex. | Solvent (parts by mass) | Mixing temperature (° C.) | Acidic compound (eq.) | Stirring temperature (° C.) | Time (hr) | Filtration temperature (° C.) | Quantitative yield (%) | Z/E ratio | Purity (%) |
|---|---|---|---|---|---|---|---|---|---|
| 2-5 | Toluene (1) | 60 | Methanesulfonic acid (0.05) | 15 | 18 | 15 | 72.3 | 1.6/98.4 | 99.2 |
| 2-6 | CPME (4) | 40 | Concentrated sulfuric acid (1.1) | 40 | 20 | 5 | 87.9 | 94.6/5.4 | 98.8 |
| 2-7 | Toluene (4) | 30 | 75 mass % aqueous sulfuric acid (1.1) | 30 | 16 | 0 | 80.4 | 95.1/4.9 | 97.9 |

Example 3

Process 1 described earlier was carried out by using two kinds of solvent as the solvent and concentrated sulfuric acid as the acidic compound. In Examples 3-1 to 3-8, toluene was used as the first Solvent A.

Example 3-1

Preparation of Compound (E)-1 Using t-Butyl Methyl Ether as the Second Solvent A 2.0 g of Compound (EZ)-1 (Z-isomer/E-isomer=50.4/49.6), 2 parts by mass of toluene and 3 parts by mass of t-butyl methyl ether (hereinafter referred to as TBME) were mixed at 40° C. 0.05 equivalent (22 mg) of concentrated sulfuric acid was added the resulting mixed solution, and the mixed solution was stirred at 15° C. for 20 hours to precipitate crystals. After the precipitation of crystals, the resulting suspension was cooled to 5° C. and stirred for 24 hours. The precipitated crystals were recovered by filtration and washed with 2 mL of a liquid mixture of toluene and n-heptane (volume ratio 1:1) to give white crystals. According to quantitative analysis, the quantitative yield of Compound (E)-1 was 70.0%, the ratio of the Z-isomer to the E-isomer was Z/E=6.2/93.8. According to qualitative analysis, the total area percentage of the peaks for the Z-isomer and the E-isomer was 98.9%.

Example 3-2

Preparation of Compound (E)-1 Using Cyclopentyl Methyl Ether as the Second Solvent A 2.0 g of Compound (EZ)-1 (Z-isomer/E-isomer=50.4/49.6), 1 part by mass of toluene and 0.05 part by mass of CPME were mixed at 40° C. 0.025 equivalent (11 mg) of concentrated sulfuric acid was added to the resulting mixed solution, and the mixed solution was stirred at 20° C. for 24 hours to precipitate crystals. After the precipitation of crystals, the resulting suspension was cooled to 10° C. and stirred for 1 hour. The precipitated crystals were recovered by filtration and washed with 2 mL of a liquid mixture of toluene and n-heptane (volume ratio 1:1) to give white crystals. According to quantitative analysis, the quantitative yield of Compound (E)-1 was 83.6%, and the ratio of the Z-isomer to the E-isomer was Z/E=0/100. According to qualitative analysis, the total area percentage of the peaks for the Z-isomer and the E-isomer was 98.7%.

Example 3-5

Preparation of the Sulfate of Compound (Z)-1 Using 1,2-Dimethoxyethane as the Second Solvent A 1.5 g of Compound (EZ)-1 (Z-isomer/E-isomer=50.4/49.6), 3 parts by mass of toluene and 0.5 part by mass of 1,2-dimethoxyethane (hereinafter referred to as DME) were mixed at 30° C. 0.5 equivalent (172 mg) of concentrated sulfuric acid was added to the resulting mixed solution, and the mixed solution was stirred for 4 hours to precipitate crystals. After precipitation of crystals, 0.6 equivalent (207 mg) of concentrated sulfuric acid was added to the resulting suspension, and the suspension was stirred for 72 hours. The suspension was cooled to 5° C. and stirred for 3 hours. The precipitated crystals were recovered by filtration and washed with 2 parts by mass of toluene to give the sulfate of Compound (Z)-1 as pale yellow crystals. According to quantitative analysis, the quantitative yield of Compound (Z)-1 was 87.3%, and the ratio of the Z-isomer to the E-isomer was Z/E=93.5/6.5. According to qualitative analysis, the total area percentage of the peaks for the Z-isomer and the E-isomer was 96.7%.

Example 3-7

Preparation of the Sulfate of Compound (Z)-1 Using t-Butyl Methyl Ether as the Second Solvent A 1.5 g of Compound (EZ)-1 (Z-isomer/E-isomer=48.8/51.2), 3 parts by mass of toluene and 3 parts by mass of TBME were mixed at 40° C. 1.1 equivalents (379 mg) of concentrated sulfuric acid was added to the mixed solution, and the mixed solution was stirred at 30° C. for 42 hours to precipitate crystals. After the precipitation of crystals, the resulting suspension was cooled to 20° C. and stirred for 1 hour. The precipitated crystals were recovered by filtration and washed with 2 parts by mass of toluene to give the sulfate of Compound (Z)-1 as pale yellow crystals. According to quantitative analysis, the quantitative yield of Compound (Z)-1 was 81.5%, and the ratio of the Z-isomer to the E-isomer was Z/E=96.0/4.0. According to qualitative analysis, the total area percentage of the peaks for the Z-isomer and the E-isomer was 96.5%.

Example 3-8

Preparation of the Sulfate of Compound (Z)-1 Using Cyclopentyl Methyl Ether as the Second Solvent A 3.0 g of Compound (EZ)-1 (Z-isomer/E-isomer=48.8/51.2), 2 parts by mass of toluene and 4.1 parts by mass of CPME were mixed at 40° C. 0.5 equivalent (344 mg) of concentrated sulfuric acid was added to the mixed solution, and the mixed solution was stirred for 8 hours to precipitate crystals. After the precipitation of crystals, 0.8 equivalent (551 mg) of concentrated sulfuric acid was added, and the suspension was stirred at 30° C. for 40 hours. The suspension was cooled to 0° C. and stirred for 2 hours. The precipitated crystals were recovered by filtration and washed with a liquid mixture of 2 parts by mass of toluene and 2 parts by mass of CPME to give the sulfate of Compound (Z)-1 as pale yellow crystals. According to quantitative analysis, the quantitative yield of Compound (Z)-1 was 89.0%, and the ratio of the Z-isomer to the E-isomer was Z/E=93.7/6.3. According to qualitative analysis, the total area percentage of the peaks for the Z-isomer and the E-isomer was 98.4%.

Examples 3-3, 3-4 and 3-6

The reaction was carried out in accordance with Example 3-2 in Examples 3-3 and 3-4, and in accordance with Example 3-5 in Example 3-6, by using various kinds of second Solvent A. The reaction conditions and the results are shown in Table 4. In the Table, the kind of the second solvent A is listed in the column titled "second solvent". "Diglyme" means diethylene glycol dimethyl ether (which also applies hereinafter).

TABLE 4

| Ex. | Second solvent A | Concentrated sulfuric acid equivalents | Quantitative yield (%) | Z/E ratio | Purity (%) |
| --- | --- | --- | --- | --- | --- |
| 3-1 | TBME | 0.05 | 70.0 | 6.2/93.8 | 98.9 |
| 3-2 | CPME | 0.025 | 83.6 | 0/100 | 98.7 |
| 3-3 | DME | 0.025 | 67.6 | 2.6/97.4 | 97.7 |
| 3-4 | Diglyme | 0.025 | 70.4 | 3.4/96.6 | 98.7 |
| 3-5 | DME | 1.1 | 87.3 | 93.5/6.5 | 96.7 |
| 3-6 | Diglyme | 1.1 | 84.6 | 93.7/6.3 | 95.3 |
| 3-7 | TBME | 1.1 | 81.5 | 96.0/4.0 | 96.5 |
| 3-8 | CPME | 1.3 | 89.0 | 93.7/6.3 | 98.4 |

Example 3-9 and 3-10, described below, used o-xylene as the first Solvent A, cyclopentyl methyl ether as the second Solvent A and various equivalents of concentrated sulfuric acid.

Example 3-9

Preparation of Compound (E)-1

2.0 g of Compound (EZ)-1 (Z-isomer/E-isomer=50.4/49.6), 1 part by mass of o-xylene and 0.5 part by mass of CPME were mixed at 50° C. 0.025 equivalent (11 mg) of concentrated sulfuric acid was added to the resulting mixed solution, and the mixed solution was stirred at 20° C. for 24 hours to precipitate crystals. After the precipitation of crystals, the resulting suspension was cooled to 5° C. and stirred for 1 hour. The precipitated crystals were recovered by filtration and washed with 1 part by mass of CPME to give white crystals. According to quantitative analysis, the quantitative yield of Compound (E)-1 was 80.7%, and the ratio of the Z-isomer to the E-isomer was Z/E=1.2/98.8. According to qualitative analysis, the total area percentage of the peaks for the Z-isomer and the E-isomer was 99.9%.

Example 3-10

Preparation of the Sulfate of Compound (Z)-1

1.5 g of Compound (EZ)-1 (Z-isomer/E-isomer=50.4/49.6), 3 parts by mass of o-xylene and 1 part by mass of CPME were mixed at 30° C. 0.5 equivalent (172 mg) of concentrated sulfuric acid was added to the resulting solution, and the mixed solution was stirred for 14 hours to precipitate crystals. After the precipitation of crystals, 0.6 equivalent (207 mg) of concentrated sulfuric acid was added to the suspension, and the suspension was stirred for 44 hours. The suspension was cooled to 20° C. and stirred for 1 hour. The precipitated crystals were recovered by filtration and washed with 2 parts by mass of o-xylene to give the sulfate of Compound (Z)-1 as pale yellow crystals. According to quantitative analysis, the quantitative yield of Compound (Z)-1 was 82.7%, and the ratio of the Z-isomer to the E-isomer was Z/E=93.1/6.9. According to qualitative analysis, the total area percentage of the peaks for the Z-isomer and the E-isomer was 95.8%.

The reaction conditions used in Examples 3-9 and 3-10 and the results of are shown in Table 5. In the Table, "o-xylene/CPME parts by mass" indicates parts by mass of o-xylene and CPME, and for example, "1/0.5" means that 1 part by mass of o-xylene and 0.5 part by mass of CPME were used.

TABLE 5

| Ex. | o-xylene/CPME parts by mass | Concentrated sulfuric acid equivalents | Quantitative yield (%) | Z/E ratio | Purity (%) |
| --- | --- | --- | --- | --- | --- |
| 3-9 | 1/0.5 | 0.025 | 80.7 | 1.2/98.8 | 99.9 |
| 3-10 | 3/1 | 1.1 | 82.7 | 93.1/6.9 | 95.8 |

Example 4

Process 2 described earlier was carried out by using various kinds of Solvent A and acidic compound.

Example 4-1

Preparation of Compound (E)-1 Using Cyclopentyl Methyl Ether as Solvent A and Hydrogen Chloride as the Acidic Compound 2.0 g of Compound (EZ)-1 (Z-isomer/E-isomer=48.8/51.2) and 3 parts by mass of CPME were mixed at 45° C. 0.05 equivalent (0.054 g) of 15.5 mass % hydrogen chloride/CPME was added to the resulting mixed solution. The mixed solution was cooled to 25° C., and 2 parts by mass of n-heptane was added dropwise over 2 hours, whereupon crystals precipitated. The resulting suspension was stirred at the same temperature for 24 hours. The precipitated crystals were recovered by filtration and washed with 2 mL of a liquid mixture of CPME and n-heptane (volume ratio 1:1) to give pale yellow crystals. According to quantitative analysis, the quantitative yield of Compound (E)-1 was 67.7%, and the ratio of the Z-isomer to the E-isomer was Z/E=0.4/99.6. According to qualitative analysis, the total area percentage of the peaks for the Z-isomer and the E-isomer was 99.3%.

Example 4-2

Preparation of Compound (E)-1 Using Toluene as Solvent A and Sulfuric Acid as the Acidic Compound 2.0 g of Compound (EZ)-1 (Z-isomer/E-isomer=50.4/49.6) and 2 parts by mass of toluene were mixed at 50° C. 0.03 equivalent (15 mg) of 85 mass % aqueous sulfuric acid was added to the resulting mixed solution. The mixed solution was stirred at 20° C. for 14 hours, whereupon crystals precipitated. 1 part by mass of n-heptane was added dropwise to the resulting suspension at the same temperature over 1 hour, and the suspension was stirred for 22 hours. The suspension was cooled to 5° C. and stirred for 2 hours. The precipitated crystals were recovered by filtration and washed with a liquid mixture of 2 parts by mass of toluene and 1 part by mass of n-heptane to give pale yellow crystals. According to quantitative analysis, the quantitative yield of Compound (E)-1 was 90.1%, and the ratio of the Z-isomer to the E-isomer was Z/E=7.1/92.9. According to qualitative analysis, the total area percentage of the peaks for the Z-isomer and the E-isomer was 99.9%.

Example 4-3

Preparation of Compound (E)-1 Using Toluene as Solvent A and p-Toluenesulfonic Acid as the Acidic Compound 2.0 g of Compound (EZ)-1 (Z-isomer/E-isomer=48.8/51.2) and 4 parts by mass of toluene were mixed at 40° C. 0.05 equivalent (42 mg) of p-toluenesulfonic acid was added to the mixed solution. The reaction solution was cooled to 15° C. and stirred for 20 hours, whereupon crystals precipitated. 1 part by mass of n-heptane was added to the resulting suspension at 20° C. over 1 hour, and the suspension was stirred at the same temperature for 24 hours. The precipitated crystals were recovered by filtration and washed with 2 mL of a liquid mixture of toluene and n-heptane (volume ratio 1:1) to give pale yellow crystals. According to quantitative analysis, the quantitative yield of Compound (E)-1 was 75.6%, and the ratio of the Z-isomer to the E-isomer was Z/E=1.8/98.2. According to qualitative analysis, the total area percentage of the peaks for the Z-isomer and the E-isomer was 98.5%.

Example 4-4

Preparation of the Sulfate of Compound (Z)-1 Using Toluene as Solvent A and Sulfuric Acid as the Acidic Compound 1.5 g of Compound (EZ)-1 (Z-isomer/E-isomer=50.4/49.6) and 4 parts by mass of toluene were mixed at 30° C. 1.1 equivalent (423 mg) of 85 mass % aqueous sulfuric acid was added to the resulting mixed solution, and the mixed solution was stirred for 16 hours, whereupon crystals precipitated. 2 parts by mass of n-heptane was added dropwise to the resulting suspension at the same temperature over 3 hours, and the suspension was stirred for 16 hours. The suspension was cooled to 0° C. and stirred for 3 hours. The precipitated crystals were recovered by filtration and washed with a liquid mixture of 2 parts by mass of toluene and 1 part by mass of n-heptane to give the sulfate of Compound (Z)-1 as pale yellow crystals. According to quantitative analysis, the quantitative yield of Compound (Z)-1 was 82.4%, and the ratio of the Z-isomer to the E-isomer was Z/E=96.6/3.4. According to qualitative analysis, the total area percentage of the peaks for the Z-isomer and the E-isomer was 98.4%.

The reaction conditions used in Examples 4-1 to 4-4 and the results are shown in Table 6. In the Table, the kind of the acidic compound is listed in the column titled "acidic compound", and the amount of the acidic compound in equivalents is listed in the column titled "equivalents".

TABLE 6

| Ex. | Acidic compound | Equivalents | Quantitative yield (%) | Z/E ratio | Purity (%) |
|---|---|---|---|---|---|
| 4-1 | 15.5 mass % hydrogen chloride/CPME | 0.05 | 67.7 | 04./99.6 | 99.3 |
| 4-2 | 85 mass % aqueous sulfuric acid | 0.03 | 90.1 | 7.1/92.9 | 99.9 |
| 4-3 | p-toluenesulfonic acid monohydride | 0.05 | 75.6 | 1.8/98.2 | 98.5 |
| 4-4 | 85 mass % aqueous sulfuric acid | 1.1 | 82.4 | 96.6/3.4 | 98.4 |

Example 5

Process 2 described earlier was carried out by using two solvents as Solvent A and various equivalents of an acidic compound. In Examples 5-1 to 5-8, toluene was used as one of the solvents, n-heptane as Solvent B, and concentrated sulfuric acid as the acidic compound.

Example 5-1

Preparation of Compound (E)-1 Using Ethyl Acetate as the Second Solvent A 2.0 g of Compound (EZ)-1 (Z-isomer/E-isomer=50.4/49.6), 1 part by mass of toluene and 0.5 part by mass of ethyl acetate were mixed at 40° C. 0.025 equivalent (12 mg) of concentrated sulfuric acid was added to the resulting mixed solution. The mixed solution was stirred at 20° C. for 24 hours to precipitate crystals. 3 parts by mass of n-heptane was added dropwise at the same temperature over 6 hours to the resulting suspension, and the suspension was stirred for 12 hours. The suspension was cooled to 5° C. and then stirred for 2 hours. The precipitated crystals were recovered by filtration and washed with a liquid mixture of 2 parts by mass of toluene and 1 part by mass of n-heptane to give pale yellow crystals. According to quantitative analysis, the quantitative yield of Compound (E)-1 was 90.5%, and the ratio of the Z-isomer to the E-isomer was Z/E=3.5/96.5. According to qualitative analysis, the total area percentage of the peaks for the Z-isomer and the E-isomer was 99.9%.

Example 5-5

Preparation of Compound (Z)-1 Using Cyclopentyl Methyl Ether as the Second Solvent A 1.5 g of Compound (EZ)-1 (Z-isomer/E-isomer=50.4/49.6), 3 parts by mass of toluene and 3 parts by mass of CPME were mixed at 30° C. 1.1 equivalent (379 mg) of concentrated sulfuric acid was added to the resulting mixed solution, and the mixed solution was stirred for 14 hours to precipitate crystals. 1 part by mass of n-heptane was added dropwise to the resulting suspension at the same temperature over 2 hours, and the suspension was stirred for 22 hours. The suspension was cooled to 15° C. and then stirred for 2 hours. The precipitated crystals were recovered by filtration and washed with a liquid mixture of 2 parts by mass of toluene and 1 part by mass of n-heptane to give the sulfate of Compound (Z)-1 as pale yellow crystals. According to quantitative analysis, the quantitative yield of Compound (Z)-1 was 89.3%, and the ratio of the Z-isomer to the E-isomer was Z/E=93.6/6.4. According to qualitative analysis, the total area percentage of the peaks for the Z-isomer and the E-isomer was 98.2%.

Examples 5-2 to 5-4 and 5-6 to 5-8

Examples 5-2 to 5-4 were carried out in accordance with Example 5-1, and Examples 5-6 to 5-8 were carried out in accordance with Example 5-5, by using various kinds of solvent and various amounts in equivalents of sulfuric acid. The reaction conditions and the results are shown in Table 7. The Table lists the kind of the second Solvent A among the two solvents used as Solvent A in the column titled "second solvent" with the amounts of the solvents in parts by mass in parentheses. In the Table, "AcOEt" denotes ethyl acetate (which also applies hereinafter), and "MEK" denotes methyl ethyl ketone.

sis, the total area percentage of the peaks for the Z-isomer and the E-isomer was 99.8%.

Example 5-10

Preparation of Compound (Z)-2

5.0 g of Compound (EZ)-1 (Z-isomer/E-isomer=48.8/51.2), 0.5 part by mass of 1,2-dichloroethane and 2.0 parts by mass of ethyl acetate were mixed at 25° C. 1.17 equivalents (475 mg) of hydrogen chloride gas was blown into the resulting mixed solution, and the mixed solution was stirred at the same temperature for 5 hours, whereupon crystals precipitated. 5 parts by mass of n-heptane was added dropwise to the resulting suspension at the same temperature over 8 hours, and the suspension was stirred for 5 hours. The

TABLE 7

| Ex. | Toluene parts by mass | Second Solvent A (parts by mass) | Sulfuric acid equivalents | Precipitation temperature (° C.) | Stirring time (hr) | n-heptane parts by mass | Stirring time after dropwise addition | Filtration temperature (° C.) | Quantitative yield (%) | Z/E ratio | Purity (%) |
|---|---|---|---|---|---|---|---|---|---|---|---|
| 5-1 | 1 | AcOEt (0.5) | 0.025 | 20 | 24 | 3 | 12 | 5 | 90.5 | 3.5/96.5 | 99.9 |
| 5-2 | 2 | CPME (0.1) | 0.025 | 15 | 20 | 2 | 18 | 15 | 87.4 | 3.5/96.5 | 98.5 |
| 5-3 | 2 | MEK (0.1) | 0.025 | 20 | 20 | 1 | 1 | 20 | 79.9 | 3.6/96.4 | 98.7 |
| 5-4 | 2 | DME (0.1) | 0.025 | 20 | 20 | 1 | 3 | 20 | 74.5 | 3.2/96.8 | 98.5 |
| 5-5 | 3 | CPME (3) | 1.1 | 30 | 14 | 1 | 22 | 15 | 89.3 | 93.6/6.4 | 98.2 |
| 5-6 | 3 | MEK (1) | 1.1 | 30 | 14 | 1 | 22 | 15 | 90.7 | 96.0/4.0 | 99.5 |
| 5-7 | 3 | DME (1) | 1.1 | 30 | 14 | 1 | 22 | 15 | 91.4 | 96.7/3.3 | 99.8 |
| 5-8 | 3 | Diglyme (1) | 1.1 | 30 | 14 | 1 | 22 | 15 | 90.1 | 96.5/3.5 | 99.0 |

In Examples 5-9 and 5-10, described below, 1,2-dichloroethane and ethyl acetate were used as Solvent A, n-heptane was used as Solvent B, and hydrogen chloride was used as the acidic compound in various equivalents.

Example 5-9

Preparation of Compound (E)-1

100 g of Compound (EZ)-1 (Z-isomer/E-isomer=48.8/51.2), 0.5 part by mass of 1,2-dichloroethane and 2.0 parts by mass of ethyl acetate were mixed at 25° C. 0.042 equivalent (340 mg) of hydrogen chloride gas was blown into the resulting mixed solution, and the mixed solution was stirred at the same temperature for 1 hour. 5 parts by mass of n-heptane was added dropwise to the mixed solution at the same temperature over 12 hours, whereupon crystals precipitated. The resulting suspension was stirred at the same temperature for 16 hours. The suspension was cooled to 5° C. and stirred for 2 hours. The precipitated crystals were recovered by filtration and washed with a liquid mixture of 3 parts by mass of n-heptane and 1 part by mass of ethyl acetate to give pale yellow crystals. According to quantitative analysis, the quantitative yield of Compound (E)-1 was 90.5%, and the ratio of the Z-isomer to the E-isomer was Z/E=1.1/98.9. According to qualitative analyprecipitated crystals were recovered by filtration and washed with a liquid mixture of 3 parts by mass of n-heptane and 1 part by mass of ethyl acetate to give Compound (Z)-2 as pale yellow crystals. According to quantitative analysis, the quantitative yield of Compound (Z)-1 was 94.4%, and the ratio of the Z-isomer to the E-isomer was Z/E=97.6/2.4. According to qualitative analysis, the total area percentage of the peaks for the Z-isomer and the E-isomer was 99.6%.

The reaction conditions used in Example 5-9 and Example 5-10 and the results are shown in Table 8. The Table lists the kind of Solvent A with the amounts of the solvents in parts by mass in parentheses.

TABLE 8

| Ex. | Solvent (parts by mass) | | HCl equivalents | n-heptane parts by mass | Quantitative yield (%) | Z/E ratio | Purity (%) |
|---|---|---|---|---|---|---|---|
| 5-9 | AcOEt (2) | EDC (0.5) | 0.042 | 5 | 90.5 | 1.1/98.9 | 99.8 |
| 5-10 | AcOEt (2) | EDC (0.5) | 1.17 | 5 | 94.4 | 97.6/2.4 | 99.6 |

Example 5-11

Preparation of Compound (E)-1

2.0 g of Compound (EZ)-1 (Z-isomer/E-isomer=50.4/49.6), 2 parts by mass of toluene and 0.1 part by mass of Diglyme were mixed at 40° C. 0.025 equivalent (11 mg) of concentrated sulfuric acid was added to the resulting mixed solution, and the mixed solution was stirred at 20° C. for 20 hours, whereupon crystals precipitated. 1 part by mass of n-heptane was added to the resulting suspension at the same temperature over 1 hour, and the suspension was stirred at 30° C. for 100 hours. The suspension was cooled to 20° C. and stirred for 1 hour. The precipitated crystals were recovered by filtration and washed with 2 mL of a liquid mixture of toluene and n-heptane (volume ratio 1:1) to give pale yellow crystals. According to quantitative analysis, the quantitative yield of Compound (E)-1 was 74.5%, and the ratio of the Z-isomer to the E-isomer was Z/E=4.0/96.0. According to qualitative analysis, the total area percentage of the peaks for the Z-isomer and the E-isomer was 98.4%.

Example 6

Preparation of Compound (E)-1 from Compound (Z)-1

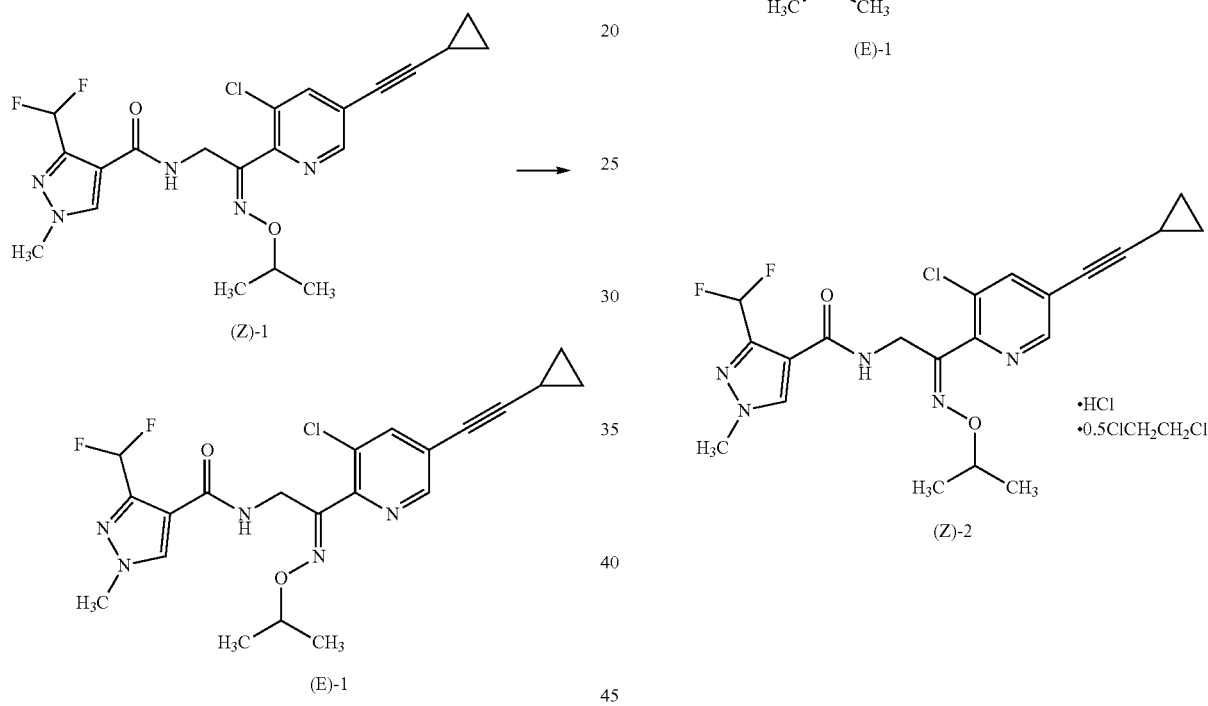

50 g of Compound (Z)-1 (Z-isomer/E-isomer=99.7/0.3) obtained in Reference Example 1 and 75 g of ethyl acetate were mixed at room temperature, and 2.25 g of 4.5 mass % hydrogen chloride/ethyl acetate (containing 0.025 equivalent of hydrogen chloride) was added to the resulting mixed solution at room temperature. The mixed solution was stirred at 40° C. for 24 hours, and 250 g of n-heptane was added dropwise at the same temperature over 5 hours. When the addition of n-heptane amounted to 100 g, crystals started to precipitate. After the dropwise addition of n-heptane, the reaction mixture was stirred at 40° C. for 4 hours and then stirred at room temperature for 16 hours. The precipitated crystals were recovered by filtration and washed with a liquid mixture of 40 g of n-heptane and 10 g of ethyl acetate to give 46.7 g of the desired product as pale yellow crystals [the quantitative yield of Compound (E)-1 was 93.4%]. According to qualitative analysis of the resulting crystals by HPLC, the area ratio of the peak for the Z-isomer to that for the E-isomer was 6.8/93.2 (Rt=10.8 minutes/12.1 minutes), and the total area percentage of the two peaks was 97.6%.

Example 7

Preparation of Compound (Z)-2 from Compound (E)-1

3.60 g of (E)-N-[2-[3-chloro-5-(cyclopropylethynyl)pyridin-2-yl]-2-(isopropoximino)ethyl]-3-(difluoromethyl)-1-methyl-1H-pyrazole-4-carboxamide (the Z-isomer/the E-isomer=6.4/93.6) and 7.20 g of 1,2-dichloroethane were mixed at 30° C. 7.22 g of 4.5 mass % hydrogen chloride/ethyl acetate (containing 1.11 equivalents of hydrogen chloride) was added to the resulting mixed solution, and the mixed solution was stirred at the same temperature, whereupon crystals precipitated. 14.4 g of n-heptane was added to the resulting suspension over 16 hours, and the suspension was stirred at 30° C. for 16 hours. The suspension was cooled to 15° C. and stirred at the same temperature for 3 hours. The precipitated crystals were recovered by filtration and washed with a liquid mixture of 7.20 g of n-heptane and 1.80 g of ethyl acetate to give 3.97 g of the desired product [the quantitative yield of Compound (Z)-1 was 89.4%]. According to qualitative analysis of the resulting crystals by HPLC, the area ratio of the peak for the Z-isomer to that for the E-isomer was 98.1/1.9 (Rt=10.8 minutes/12.1 minutes), and the total area percentage of the two peaks was 97.5%.

Example 8

Preparation of Compound (Z)-1 from Compound (E)-1

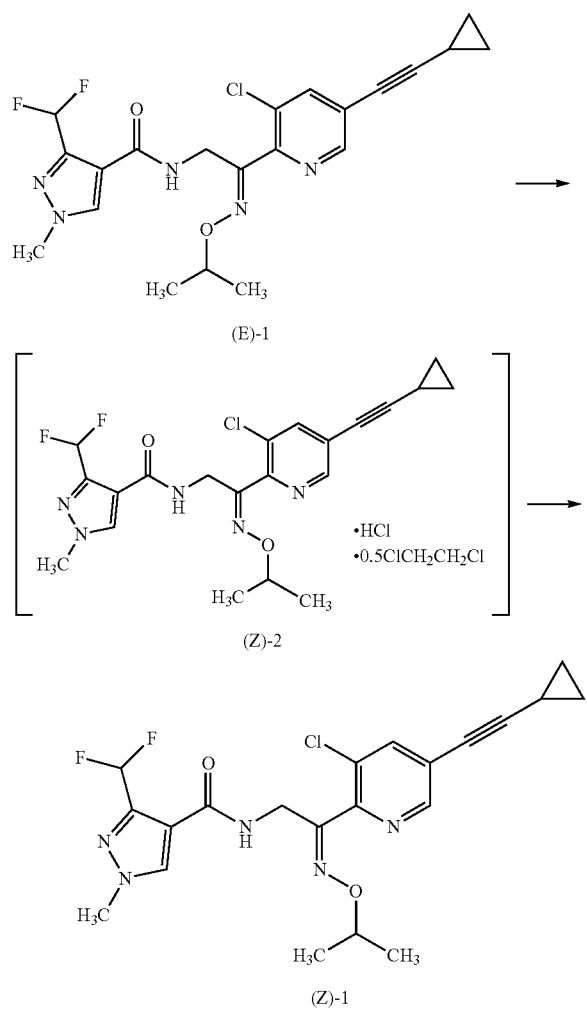

3.60 g of Compound (E)-1 (Z-isomer/E-isomer=0.1/99.9) and 7.20 g of 1,2-dichloroethane were mixed at 30° C. 7.22 g of 4.5 mass % hydrogen chloride/ethyl acetate (containing 1.11 equivalents of hydrogen chloride) was added to the resulting mixed solution, and the mixed solution was stirred at the same temperature for 4 hours, whereupon crystals precipitated. 14.4 g of n-heptane was added dropwise to the resulting suspension over 8 hours, and the suspension was stirred at 30° C. for 8 hours. The suspension was cooled to 0° C. and stirred at the same temperature for 2 hours. 10.8 g of water was added dropwise to the suspension at 0° C., and 6.0 mL of 2.0 mol/L aqueous potassium carbonate was added dropwise. The reaction solution was stirred at 0° C. for 2 hours, and the precipitated crystals were recovered by filtration and washed with 10.8 g of water and then with a liquid mixture of 2.40 g of water and 4.80 g of ethanol to give 2.93 g of the desired product as white crystals (yield 79.6%). According to qualitative analysis of the resulting crystals by HPLC, the area ratio of the peak for the Z-isomer to that for the E-isomer was 99.0/1.0 (Rt=10.8 minutes/12.1 minutes), and the total area percentage of the two peaks was 98.5%.

Example 9

The reaction in Process 1 described earlier was carried out by using various kinds of solvents and various kinds and equivalents of acidic compounds and a small amount of a salt of Compound (Z)-1 to promote crystallization.

Example 9-1

Preparation of the Hydrochloride of Compound (Z)-1 [Hereinafter Referred to as (Z)-3] Using CPME as the Solvent and Hydrogen Chloride as the Acidic Compound 2.0 g of Compound (EZ)-1 (Z-isomer/E-isomer=48.8/51.2) and 1.45 parts by mass of CPME were mixed at 50° C. 1.2 equivalents (1.3 g) of 15.5 mass % hydrogen chloride/CPME was added to the resulting mixed solution at 50° C. 2.0 mg of Compound (Z)-2 prepared in Reference Example 3 was added to the mixed solution at the same temperature, and the mixed solution was stirred for 20 minutes to precipitate crystals. The resulting suspension was cooled to 25° C. and stirred for 20 hours. The precipitated crystals were recovered by filtration and washed with 2 mL of the same solvent as used in the reaction, CPME, to give pale red crystals. According to quantitative analysis, the quantitative yield of Compound (Z)-1 was 73.0%, and the ratio of the Z-isomer to the E-isomer was Z/E=90.8/9.2. According to qualitative analysis, the total area percentage of the peaks for the Z-isomer and the E-isomer was 97.8%.

Examples 9-2 and 9-3

The reaction was carried out in accordance with Example 9-1 by using various kinds of solvent and various kinds and equivalents of the acidic compound. The reaction conditions and the results are shown in Table 9. The Table lists the kind of the solvent in the column titled "solvent" with the amount of the solvent in parts by mass in parentheses, and the kind of the acidic compound in the column titled "acidic compound" with the amount of the acidic compound in equivalents in parentheses.

TABLE 9

| Ex. | Solvent (parts by mass) | Mixing temperature (° C.) | Acidic compound (equivalents) | Time (hr) | Filtration temperature (° C.) | Quantitative yield (%) | Z/E ratio | Purity (%) |
|---|---|---|---|---|---|---|---|---|
| 9-1 | CPME (2) | 50 | 15.5 mass % hydrogen chloride/CPME (1.2) | 0.33 | 25 | 73.0 | 90.8/9.2 | 97.8 |
| 9-2 | Toluene (6) | 40 | Methanesulfonic acid (1.1) | 16 | 20 | 82.1 | 94.9/5.1 | 99.9 |

TABLE 9-continued

| Ex. | Solvent (parts by mass) | Mixing temperature (° C.) | Acidic compound (equivalents) | Time (hr) | Filtration temperature (° C.) | Quantitative yield (%) | Z/E ratio | Purity (%) |
|---|---|---|---|---|---|---|---|---|
| 9-3 | CPME (8) | 50 | Methanesulfonic acid (1.1) | 16 | 30 | 89.1 | 94.8/5.2 | 99.9 |

Example 10

The reaction in Process 2 described earlier was carried out by using various kinds of solvent, various kinds and equivalents of acidic compound and a small amount of a salt of Compound (Z)-1 to promote crystallization.

Example 10-1

Preparation of Compound (Z)-3 Using CPME as Solvent A and Hydrogen Chloride as the Acidic Compound 2.0 g of Compound (EZ)-1 (Z-isomer/E-isomer=48.8/51.2), 2.45 parts by mass, relative to the starting material, of CPME were mixed at 45° C. 1.2 equivalents (1.3 g) of 15.5 mass % hydrogen chloride/CPME was added to the resulting mixed solution. 2.0 mg of compound (Z)-3 prepared in Reference Example 3 was added to the mixed solution at the same temperature, and the mixed solution was stirred for 20 minutes to precipitate crystals. 2 parts by mass of n-heptane was added to the resulting suspension over 2 hours, and the suspension was stirred for 24 hours. The precipitated crystals were recovered by filtration and washed with CPME (2 mL) to give pale yellow crystals. According to quantitative analysis, the quantitative yield of Compound (Z)-1 was 79.1%, and the ratio of the Z-isomer to the E-isomer was Z/E=95.6/4.4. According to qualitative analysis, the total area percentage of the peaks for the Z-isomer and the E-isomer was 99.2%.

Example 10-2

Preparation of the Sulfate of Compound (Z)-1 Using Toluene and Ethyl Acetate as Solvent A and Concentrated Sulfuric Acid as the Acidic Compound 2.0 g of Compound (EZ)-1 (Z-isomer/E-isomer=50.4/49.6), 2 parts by mass of toluene and 3 parts by mass of ethyl acetate were mixed at 30° C. 1.1 equivalents (507 mg) of concentrated sulfuric acid was added to the resulting mixed solution. 2.0 mg of the sulfate of Compound (Z)-1 prepared in Reference Example 4 was added to the mixed solution at the same temperature, and the mixed solution was stirred for 14 hours to precipitate crystals. 1 part by mass of n-heptane was added to the resulting suspension at the same temperature over 24 hours, and the suspension was stirred for 18 hours. The suspension was cooled to 0° C. and stirred for 4 hours. The precipitated crystals were recovered by filtration and washed with a liquid mixture of 2 parts by mass of toluene and 1 part by mass of n-heptane to give pale yellow crystals. According to quantitative analysis, the quantitative yield of Compound (Z)-1 was 88.3%, and the ratio of the Z-isomer to the E-isomer was Z/E=97.0/3.0. According to qualitative analysis, the total area percentage of the peaks for the Z-isomer and the E-isomer was 99.8%.

The reaction conditions used in Examples 10-1 and 10-2 and the results are shown in Table 10. The Table lists the kind of Solvent A in the column titled "solvent" with the amount of the solvent in parentheses and the kind of acidic compound in the column titled "acidic compound" with the amount of the acidic compound in parentheses.

TABLE 10

| Ex. | Solvent (parts by mass) | | Mixing temperature (° C.) | Acidic compound (equivalents) | n-heptane parts by mass | Stirring time after dropwise addition (hr) | Filtration temperature (° C.) | Quantitative yield (%) | Z/E ratio | Purity (%) |
|---|---|---|---|---|---|---|---|---|---|---|
| 10-1 | CPME (3) | — | 45 | 15.5 mass % hydrogen chloride/CPME (1.2) | 2 | 24 | 45 | 79.1 | 95.6/4.4 | 99.2 |
| 10-2 | Toluene (2) | AcOEt (3) | 30 | Concentrated sulfuric acid (1.1) | 4 | 18 | 0 | 88.3 | 97.0/3.0 | 99.8 |

Example 11

Preparation of Compound (Z)-3 from Compound (E)-1

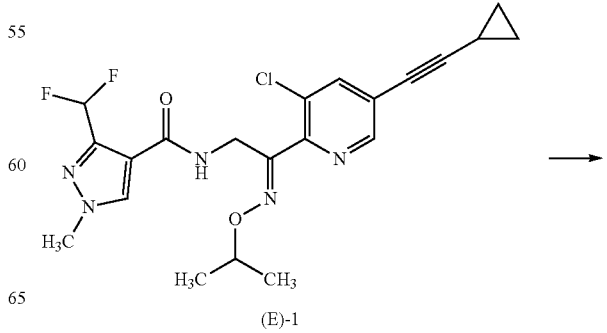

(E)-1

-continued

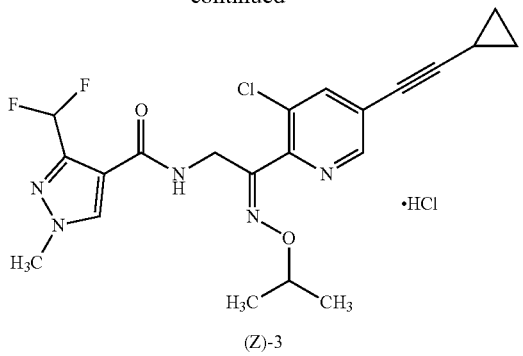

(Z)-3

3.60 g of Compound (E)-1 (Z-isomer/E-isomer=0.1/99.9) and 7.20 g of toluene were mixed at 30° C. 7.39 g of 4.5 mass % hydrogen chloride/ethyl acetate (containing 1.14 equivalent of hydrogen chloride) was added to the resulting mixed solution, and the mixed solution was stirred at the same temperature for 2 hours. 36 mg of Compound (Z)-3 was added to the mixed solution, and the mixed solution was stirred for 2 hours, whereupon crystals precipitated. 14.4 g of n-heptane was added dropwise to the resulting suspension over 16 hours, and the suspension was stirred at 30° C. for 5 hours. The suspension was cooled to 15° C. and stirred for 3 hours. The precipitated crystals were recovered by filtration and washed with a liquid mixture of 7.20 g of n-heptane and 1.80 g of ethyl acetate to give 3.72 g of the desired product as pale yellow crystals [the quantitative yield of Compound (Z)-1 was 92.2%]. According to qualitative analysis of the resulting crystals by HPLC, the area ratio of the peak for the Z-isomer to that for the E-isomer was 98.1/1.9 (Rt=10.8 minutes/12.1 minutes), and the total area percentage of the two peaks was 97.6%.

7.5 mg of the crystals and 5.0 mL of toluene were mixed at room temperature, and 6.0 mL of 0.005 mol/L aqueous sodium hydroxide was added. The resulting solution was stirred at the same temperature for 30 minutes and was separated into an aqueous layer and an organic layer. The organic layer was stirred with 3.0 mL of 0.005 mol/L aqueous sodium hydroxide for 30 minutes and separated into an aqueous layer and an organic layer. The aqueous layers were combined. According to IC analysis, the chloride ion content was 7.1 mass %, and the molar ratio of Compound (Z)-1 to hydrogen chloride was 1:1.

Example 12

Preparation of Compound (Z)-1 from Compound (EZ)-1

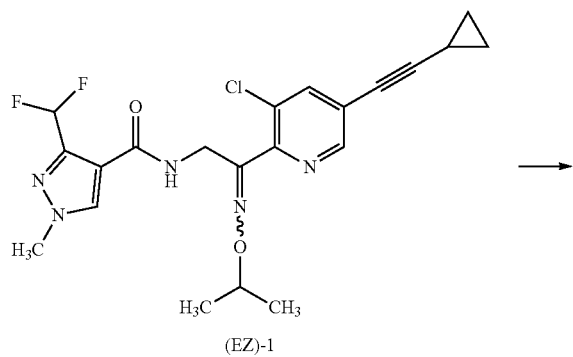

(EZ)-1

-continued

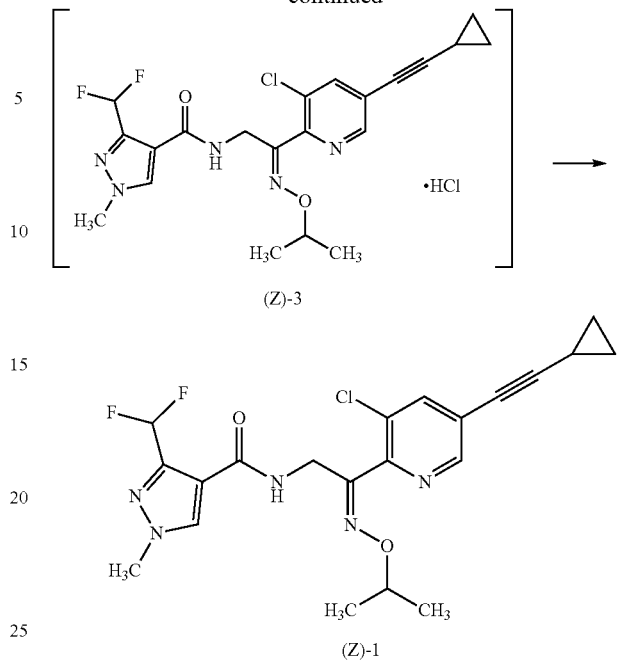

4.04 g of Compound (EZ)-1 (Z-isomer/E-isomer=42.4/57.6) and 8.08 g of toluene were mixed at 25° C. 8.93 g of 4.4 mass % hydrogen chloride/ethyl acetate (containing 1.2 equivalents of hydrogen chloride) was added to the resulting mixed solution, and the mixed solution was stirred at the same temperature for 30 minutes. 2.0 mg of Compound (Z)-3 was added to the mixed solution, and the mixed solution was stirred for 6 hours, whereupon crystals precipitated. 18.2 g of n-heptane was added dropwise to the resulting suspension over 8 hours, and the suspension was stirred at 25° C. for 9 hours. The suspension was cooled to 0° C. and stirred for 1 hour. 20.2 g of water was added dropwise to the suspension, and 18.2 g of ethyl acetate was added. 6.74 g of 8.0 mass % aqueous sodium hydroxide was added dropwise at 0° C., and the reaction solution was stirred at the same temperature for 30 minutes. After the stirring, the organic layer was separated at 25° C. and washed with 12.1 g of water, and the solvent was distilled off under reduced pressure. The resulting residue was mixed with 12.1 g of toluene, and the solvent was distilled off under reduced pressure. The resulting residue was mixed with 16.16 g of toluene at room temperature and heated to 70° C. 8.08 g of n-heptane was added to the resulting mixed solution, and the mixed solution was stirred at the same temperature for 30 minutes. The mixed solution was cooled to 40° C., and 4.0 mg of Compound (Z)-1 was added at the same temperature. On cooling to 20° C., crystals precipitated from the mixed solution. The resulting suspension was stirred at the same temperature for 12 hours and then cooled to 0° C. The suspension was stirred at the same temperature for 5 hours, and the precipitated crystals were recovered by filtration and washed with a liquid mixture of 4.04 g of toluene and 2.02 g of n-heptane to give 3.36 g of the desired product as pale yellow crystals (yield 83.3%). According to qualitative analysis of the resulting crystals by HPLC, the area ratio of the peak for the Z-isomer to that for the E-isomer was 97.3/2.7 (Rt=10.8 minutes/12.1 minutes), and the total area percentage of the two peaks was 98.2%.

Example 13

Preparation of Compound (Z)-1 from Compound (EZ)-1

5.04 g of Compound (EZ)-1 (Z-isomer/E-isomer=50.4/49.6), 3 parts by mass of toluene and 1 part by mass of DME were mixed at 30° C. 1.1 equivalents (1.27 g) of concentrated sulfuric acid was added, and the resulting mixed solution was stirred at the same temperature for 30 minutes. 1.5 mg of the sulfate of Compound (Z)-1 was added to the mixed solution, and the mixed solution was stirred for 20.5 hours, whereupon crystals precipitated. The resulting suspension was cooled to 0° C. and stirred for 2.5 hours. 5 parts by mass of water was added dropwise to the suspension, and 3 parts by mass of toluene was added. 2.2 equivalents (13.99 g) of 8.0 mass % aqueous sodium hydroxide was added dropwise at 0° C., and the reaction solution was stirred at the same temperature for 30 minutes. After the stirring, the organic layer was separated at 25° C. and washed with 3 parts by mass of water twice, and the solvent was distilled off under reduced pressure. The resulting residue was mixed with 4 parts by mass of toluene and 2 parts by mass of n-heptane at 70° C. and then cooled to 40° C., and the resulting mixed solution was stirred with 5.0 mg of Compound (Z)-1 at the same temperature for 30 minutes to precipitate crystals. The resulting suspension was cooled to 0° C. and stirred for 13 hours. The precipitated crystals were recovered by filtration and washed with a liquid mixture of 1 part by mass of toluene and 0.5 part by mass of n-heptane to give 3.96 g of Compound (Z)-1 as pale yellow crystals (yield 78.6%). According to qualitative analysis, the area ratio of the peak for the Z-isomer to that for the E-isomer was 97.1/2.9, and the total area percentage of the two peaks was 99.2%.

Example 14

The reaction in Example 1 was carried out, and after recovery of the precipitated crystals by filtration, the oximino compound in the filtrate was used as the starting material.

Example 14-1

Preparation of Compound (E)-1

The procedure in Example 1-1 was followed by using 10 g of Compound (EZ)-1 (Z-isomer/E-isomer=48.8/51.2), 1 part by mass of 1,2-dichloroethane, 0.450 g of 4.5 mass % hydrogen chloride/ethyl acetate (containing 0.025 equivalent of hydrogen chloride) and 25.4 g of ethyl acetate to give pale yellow crystals (8.45 g). According to quantitative analysis, the quantitative yield of Compound (E)-1 was 82.8%. According to qualitative analysis, the area ratio of the peak for the Z-isomer to that for the E-isomer was 1.4/98.6, and the total area percentage of the two peaks was 99.9%. According to quantitative analysis of the filtrate, the filtrate contained a mixture of the Z-isomer and the E-isomer (the ratio of the Z-isomer to the E-isomer was Z/E=67.8/32.2).

The filtrate containing 1.62 g of Compound (EZ)-1 (Z-isomer/E-isomer=67.8/32.2) was concentrated under reduced pressure, and the procedure mentioned above was carried out using 1 part by mass of 1,2-dichloroethane, 0.025 equivalent (0.073 g) of 4.5 mass % hydrogen chloride/ethyl acetate and 4.11 g of ethyl acetate to give 1.31 g of pale yellow crystals. According to quantitative analysis, the quantitative yield of Compound (E)-1 was 12.5% [relative to 10 g of Compound (EZ)-1], and the ratio of the Z-isomer to the E-isomer was Z/E=1.8/98.2. According to qualitative analysis, the total area percentage of the peaks for the Z-isomer and the E-isomer was 99.7%.

The reaction was repeated using the filtrate to give Compound (E)-1 in a total yield of 95.3%.

Examples 14-2 to 14-3

The reaction was carried out in accordance with Example 14-1 by using various amounts of hydrogen chloride/ethyl acetate. The results are tabulated in the same manner as in Table 2.

TABLE 11

| Ex. | | HCl equivalents (eq.) | Quantitative yield (%) | Z/E ratio | Purity (%) |
|---|---|---|---|---|---|
| 14-1 | — | 0.025 | 82.8 | 1.4/98.6 | 99.9 |
| | Filtrate | 0.025 | 12.5 | 1.8/98.2 | 99.7 |
| | Total | — | 95.3 | 1.5/98.5 | 99.9 |
| 14-2 | — | 0.05 | 81.1 | 5.4/94.6 | 99.7 |
| | Filtrate | 0.05 | 12.6 | 2.8/97.8 | 98.5 |
| | Total | — | 93.7 | 5.1/94.9 | 99.5 |
| 14-3 | — | 0.75 | 73.3 | 97.1/2.9 | 99.9 |
| | Filtrate | 0.75 | 17.8 | 96.5/3.5 | 99.9 |
| | Total | — | 91.1 | 96.9/3.1 | 99.9 |

Reference Example 1

Preparation of Compound (Z)-1

Crystals prepared in accordance with Synthetic Example 27 in JP-A-2016-011286 were qualitatively analyzed by HPLC, and a peak was detected at a retention time of 10.8 min.

m.p.: 105 to 107° C.

$^1$H-NMR: δ8.55-8.45 (m, 2H), 8.14 (s, 1H), 7.95-7.90 (m, 1H), 7.16 (t, J=54.3 Hz, 1H), 4.26 (d, J=6.0 Hz, 2H), 4.30-4.20 (m, 1H), 3.88 (s, 3H), 1.65-1.55 (m, 1H), 1.23 (d, J=6.6 Hz, 6H), 0.95-0.85 (m, 2H), 0.80-0.73 (m, 2H).

Vapor diffusion crystallization using n-hexane from a mixture of 1 mg of the crystals and 1 mL of chloroform afforded column crystals. X-ray single-crystal structural analysis of the crystals under the following conditions identified the crystals as Compound (Z)-1 having a Z-configured oximino group.

[Analysis Conditions]

Instrument: SMART APEXII ULTRA (Bruker AXS K.K.)

X-ray: CuKα (50 kV, 24 mA)

Measuring temperature: −75° C.

Reference Example 2

Preparation of Compound (EZ)-1

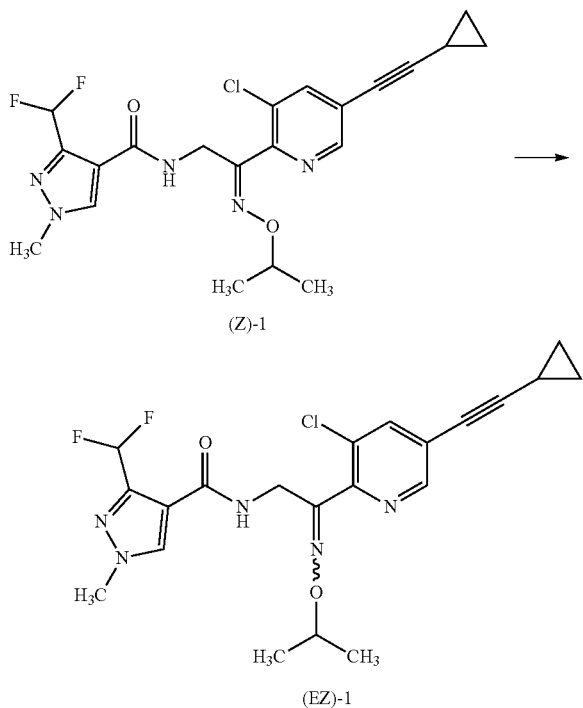

120 g of Compound (Z)-1 (Z-isomer/E-isomer=99.7/0.3) prepared in Reference Example 1 and 180 g of ethyl acetate were mixed at room temperature 5.40 g (0.025 equivalent) of 4.5 mass % hydrogen chloride/ethyl acetate was added to the resulting mixed solution at room temperature, and the mixed solution was stirred at the same temperature for 48 hours. After the reaction, 180 g of water and 369 g (0.1 equivalent) of potassium carbonate were added at room temperature, and the reaction solution was stirred at the same temperature for 30 minutes. The organic layer was separated, washed with saturated aqueous sodium chloride (100 mL×2), dried over anhydrous sodium sulfate and concentrated under reduced pressure. The resulting residue was mixed with 1,800 g of n-heptane and 180 g of ethyl acetate at room temperature and stirred at the same temperature for 24 hours. The precipitated crystals were recovered by filtration and washed with a liquid mixture of 200 g of n-heptane and 20 g of ethyl acetate to give 114.7 g of milk white crystals. The LC/MS spectrum of the crystals showed two peaks (retention times: 3.5 minutes and 4.0 minutes) both having an MS peak at an m/z ratio of 450 (M+). Qualitative analysis of the crystals by HPLC gave two peaks, and the total area percentage of the two peaks was 99.8%. One of the peaks had a retention time of 10.8 minutes (the area percentage of 51.6%), and the other had a retention time of 12.1 minutes (the area percentage of 48.2%). The peak at a retention time of 10.8 minutes is attributed to the Z-isomer used as the starting material, and the peak at a retention time of 12.1 minutes was identified as the E-isomer by the above-mentioned LC/MS analysis and $^1$H-NMR data. Thus, in qualitative analysis by HPLC, the retention time of the Z-isomer is 10.8 minutes, and the retention time of the E-isomer is 12.1 minutes.

The $^1$H-NMR data for (E)-N-[2-[3-chloro-5-(cyclopropylethynyl)pyridin-2-yl]-2-(isopropoximino)ethyl]-3-(difluoromethyl)-1-methyl-1H-pyrazole-4-carboxamide are shown below.

$^1$H-NMR: δ8.42 (d, J=1.8 Hz, 1H), 8.30 (t, J=5.7 Hz, 1H), 8.03 (s, 1H), 7.91 (d, J=1.8 Hz, 1H), 7.10 (t, J=54.3 Hz, 1H), 4.42 (d, J=5.7 Hz, 2H), 4.35 (sep, J=6.6 Hz, 1H), 3.83 (s, 3H), 1.60-1.50 (m, 1H), 1.23 (d, J=6.6 Hz, 6H), 0.95-0.85 (m, 2H), 0.80-0.73 (m, 2H).

Reference Example 3

Preparation of the Hydrochloride of Compound (Z)-1

1.80 g of Compound (Z)-1 (Z-isomer/E-isomer=99.7/0.3) and 3.60 g of toluene were mixed at 25° C. 3.61 g of hydrogen chloride in ethyl acetate (4.5 mass %) (containing 1.11 equivalent of hydrogen chloride) was added to the resulting mixed solution, and the mixed solution was stirred at the same temperature for 30 minutes. 18 mg of 1,2-dichloroethane hemisolvate of Compound (Z)-1 was added to the mixed solution, and the mixed solution was stirred for 16 hours, whereupon crystals precipitated. The resulting suspension was cooled to 15° C. and stirred for 4 hours. The precipitated crystals were recovered by filtration and washed with a liquid mixture of 2.70 g of n-heptane and 0.90 g of ethyl acetate to give 0.86 g of the desired product as pale yellow crystals [the quantitative yield of Compound (Z)-1 was 40.7%]. According to qualitative analysis of the resulting crystals by HPLC, the area ratio of the peak for the Z-isomer to that for the E-isomer was 98.4/1.6 (Rt=10.8 minutes/12.1 minutes), and the total area percentage of the two peaks was 96.3%.

Reference Example 4

Preparation of the Sulfate of Compound (Z)-1

5.0 g of Compound (Z)-1 (Z-isomer/E-isomer=99.7/0.3) and 5 parts by mass of ethyl acetate were mixed at 0° C. 1.0 equivalent (1.13 g) of concentrated sulfuric acid was added to the resulting mixed solution, and the mixed solution was stirred at the same temperature for 30 minutes, whereupon crystals precipitated. The precipitated crystals were recovered by filtration and washed with a liquid mixture of 2 parts by ethyl acetate and 2 parts by mass of n-heptane to give 6.00 g of white crystals. According to quantitative analysis, the quantitative yield of Compound (Z)-1 was 94.6%, and the ratio of the Z-isomer to the E-isomer was Z/E=98.6/1.4. According to qualitative analysis, the total area percentage of the peaks for the Z-isomer and the E-isomer was 99.9%.

1.0 mg of the crystals and 2.0 mL of toluene were mixed at room temperature, then stirred with 10 mL of 0.005 mol/L aqueous sodium hydroxide at the same temperature for 30 minutes and separated into an aqueous layer and an organic layer. According to IC analysis of the aqueous layer, the aqueous layer had a sulfate ion content of 17.9 mass % and contained Compound (Z)-1 and sulfuric acid in a 1:1 molar ratio.

$^1$H-NMR: δ8.51 (d, J=6.0 Hz, 1H), 8.50 (t, J=1.5 Hz, 1H), 8.16 (s, 1H), 7.95 (t, J=1.5 Hz, 1H), 7.41 (brs, 2H, sulfate), 7.17 (t, J=54.6 Hz, 1H), 4.30-4.20 (m, 3H), 3.90 (s, 3H), 1.65-1.55 (m, 1H), 1.10 (d, J=6.0 Hz, 6H), 1.00-0.90 (m, 2H), 0.85-0.75 (m, 2H).

Reference Example 5

Preparation of the Methanesulfonate of Compound (Z)-1

20 g of Compound (Z)-1 (Z-isomer/E-isomer=99.7/0.3) and 3 parts by mass of ethyl acetate were mixed at 0° C. 1.0 equivalent (4.27 g) of methanesulfonic acid was added to the resulting mixed solution, and the mixed solution was stirred at the same temperature for 1 hour, whereupon crystals precipitated. The precipitated crystals were recovered by filtration and washed with a liquid mixture of 2 parts by mass of ethyl acetate and 2 parts by mass of n-heptane to give white crystals. According to quantitative analysis, the quantitative yield of Compound (Z)-1 was 88.4%, and the ratio of the Z-isomer to the E-isomer was Z/E=99.1/0.9. According to qualitative analysis, the total area percentage of the peaks for the Z-isomer and the E-isomer was 98.2%.

$^1$H-NMR: δ8.90 (brs, 1H, methanesulfonate), 8.54 (d, J=6.0 Hz, 1H), 8.50 (t, J=1.5 Hz, 1H), 8.17 (s, 1H), 7.96 (d, J=1.5 Hz, 1H), 7.17 (t, J=54.0 Hz, 1H), 4.30-4.20 (m, 3H), 3.90 (s, 3H), 2.40 (s, 3H, methanesulfonate), 1.65-1.55 (m, 1H), 1.10 (d, J=6.0 Hz, 6H), 1.00-0.90 (m, 2H), 0.85-0.75 (m, 2H).

Reference Example 6

Preparation of the p-Toluenesulfonate of Compound (Z)-1

11.05 g of p-toluenesulfonic acid monohydrate and 10 parts by mass of toluene were mixed at room temperature. The resulting mixed solution was stirred under reflux using a Dean Stark apparatus for 2 hours to azeotropically remove water, and then toluene was added until the total weight of the solution became 100 g.

3.0 g of Compound (Z)-1 (Z-isomer/E-isomer=99.7/0.3) and 2 parts by mass of ethyl acetate were mixed at 0° C. 12.63 g of the mixed solution prepared above (containing 1.1 equivalents of p-toluenesulfonic acid) was added to the mixed solution, and the resulting mixed solution was stirred at the same temperature for 30 minutes, whereupon crystals precipitated. The precipitated crystals were recovered by filtration and washed with a liquid mixture of 2 parts by mass of ethyl acetate and 2 parts by mass of n-heptane to give 2.15 g of pale yellow crystals. According to quantitative analysis, the quantitative yield of Compound (Z)-1 was 45.0%, and the ratio of the Z-isomer to the E-isomer was Z/E=95.5/4.5. According to qualitative analysis, the total area percentage of the peaks for the Z-isomer and the E-isomer was 98.7%.

$^1$H-NMR: δ12.20 (brs, 1H, p-toluenesulfonate), 8.54 (d, J=6.0 Hz, 1H), 8.50 (t, J=1.5 Hz, 1H), 8.19 (s, 1H), 7.96 (t, J=1.5 Hz, 1H), 7.52 (d, J=8.1 Hz, 2H, p-toluenesulfonate), 7.18 (t, J=54.9 Hz, 1H), 7.15 (d, J=8.1 Hz, 2H, p-toluenesulfonate), 4.30-4.20 (m, 3H), 3.90 (s, 3H), 2.30 (s, 3H, p-toluenesulfonate), 1.65-1.55 (m, 1H), 1.10 (d, J=6.0 Hz, 6H), 1.00-0.90 (m, 2H), 0.85-0.75 (m, 2H).

Reference Example 7

Preparation of the Oxalate of Compound (Z)-1

1.0 g of Compound (Z)-1 (Z-isomer/E-isomer=99.7/0.3) and 3 parts by mass of toluene were mixed at 0° C. 1.0 equivalent (200 mg) of oxalic acid was added to the resulting mixed solution, and the mixed solution was stirred at the same temperature for 20 hours, whereupon crystals precipitated. The precipitated crystals were recovered by filtration and washed with 1 part by mass of toluene to give 989 mg of white crystals. According to quantitative analysis, the quantitative yield of Compound (Z)-1 was 80.0%, and the ratio of the Z-isomer to the E-isomer was Z/E=99.3/0.7). According to qualitative analysis, the total area percentage of the peaks for the Z-isomer and the E-isomer was 99.8%.

50 mg of the crystals were mixed with 5.0 mL of methanol at room temperature. 0.005 mol/L aqueous sodium hydroxide was added to the resulting mixed solution. Analysis of the resulting mixed solution by IC confirmed that the oxalate ion content was 17.5 mass %, and the molar ratio of compound (Z)-1 to sulfuric acid was 1:1.

$^1$H-NMR: δ8.55-8.45 (m, 2H), 8.16 (s, 1H), 8.00-7.95 (m, 1H), 7.18 (t, J=54.3 Hz, 1H), 4.30-4.20 (m, 3H), 3.90 (s, 3H), 1.65-1.55 (m, 1H), 1.10 (d, J=6.0 Hz, 6H), 1.00-0.90 (m, 2H), 0.85-0.75 (m, 2H).

Reference Example 8

Powder X-Ray Diffraction of Compound (E)-1

Powder X-ray diffraction of Compound (E)-1 obtained in Example 1-1 was performed. The powder X-ray diffraction spectrum chart is shown in FIG. 1. In the powder X-ray diffraction spectrum, the following peak values were obtained as characteristic peaks. Peak values in the powder X-ray diffraction usually have a margin of error of ±0.2.

Diffraction angle (2θ): 7.35, 8.00, 12.83, 14.62, 15.26, 15.93, 16.35, 16.64, 18.00, 18.22, 18.61, 20.66, 22.07, 22.64, 23.15, 23.40, 23.96, 24.77, 25.55, 25.75 and 28.24.

Reference Example 9

Powder X-Ray Diffraction of Compound (Z)-2

Figure 2:
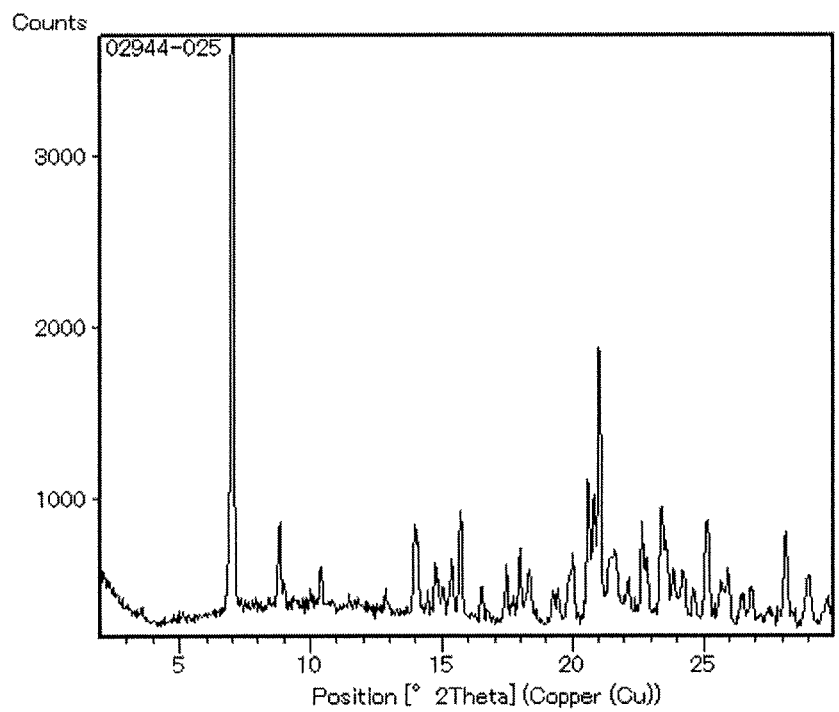
FIG. 2 A powder X-ray diffraction chart of 1,2-dichloroethane hemisolvate of (Z)—N-[2-[3-chloro-5-(cyclopropylethynyl)pyridin-2-yl]-2-(isopropoximino)ethyl]-3-(difluoromethyl)-1-methyl-1H-pyrazole-4-carboxamide hydrochloride obtained in Example 1-2.

Powder X-ray of Compound (Z)-2 obtained in Example 1-2 was performed. The powder X-ray diffraction spectrum chart is shown in FIG. 2. In the powder X-ray diffraction spectrum chart, the following peak values were obtained as characteristic peaks. Peak values in the powder X-ray diffraction usually have a margin of error of ±0.2.

Diffraction angle (2θ): 7.02, 8.85, 13.96, 15.39, 15.71, 17.45, 18.00, 18.34, 20.03, 20.62, 20.83, 21.05, 21.67, 22.66, 22.86, 23.40, 23.61, 23.86, 25.13, 25.98 and 28.14.

Reference Example 10

Powder X-Ray Diffraction of Compound (Z)-3

Figure 3:
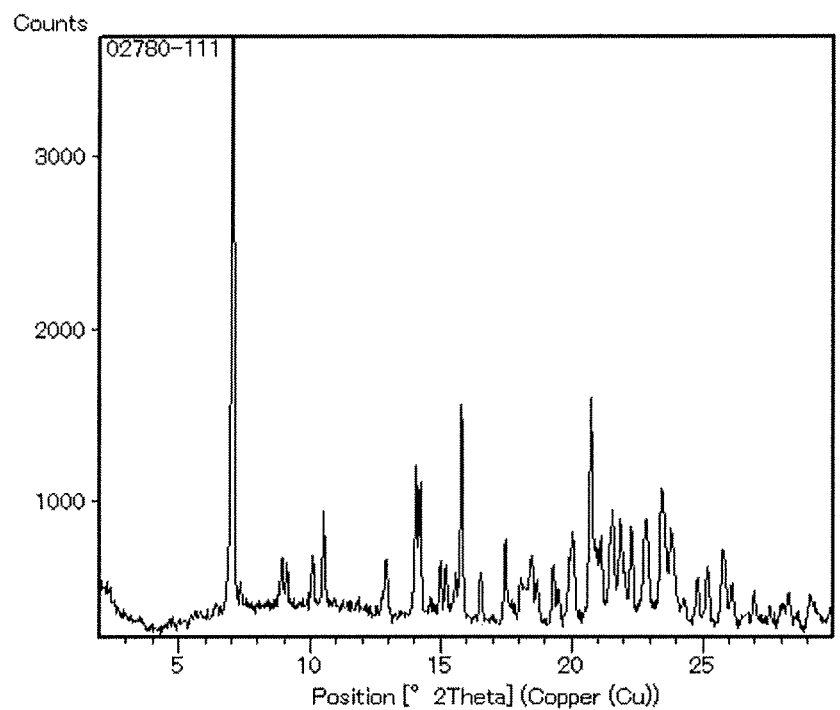
FIG. 3 A powder X-ray diffraction chart of (Z)—N-[2-[3-chloro-5-(cyclopropylethynyl)pyridin-2-yl]-2-(isopropoximino)ethyl]-3-(difluoromethyl)-1-methyl-1H-pyrazole-4-carboxamide hydrochloride obtained in Example 11.

Powder X-ray Diffraction of Compound (Z)-3 obtained in Example 11 was performed. The powder X-ray diffraction spectrum chart is shown in FIG. 3. In the powder X-ray diffraction spectrum chart, the following peak values were obtained as characteristic peaks. Peak values in the powder X-ray diffraction usually have a margin of error of ±0.2.

Diffraction angle (2θ): 7.05, 10.48, 14.03, 14.21, 15.79, 17.47, 18.47, 20.02, 20.70, 21.09, 21.56, 21.85, 22.26, 22.83, 23.42, 23.80, 25.17 and 25.76.

Reference Example 11

Powder X-Ray Diffraction of Compound (Z)-1

Figure 4:
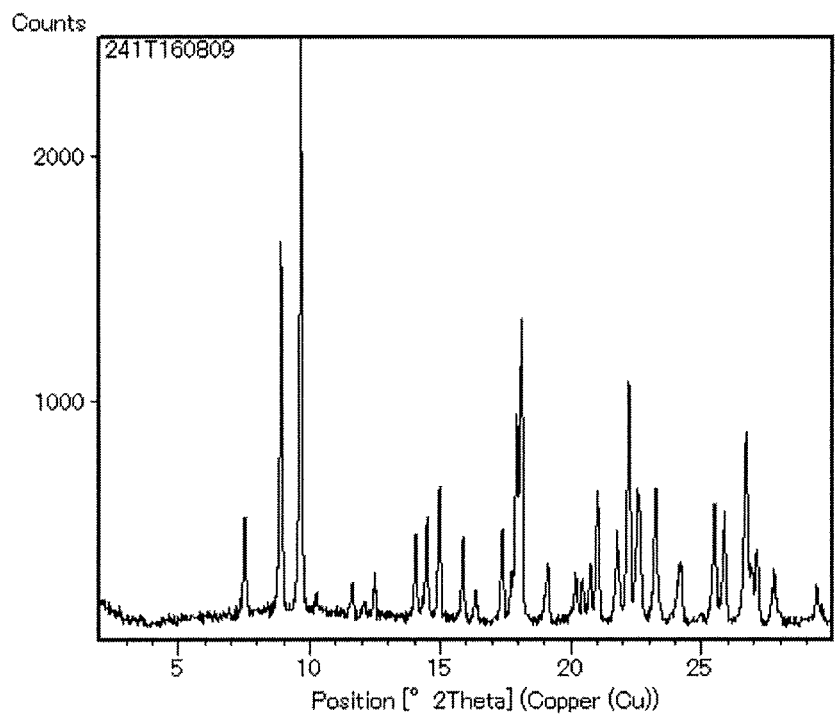
FIG. 4 A powder X-ray diffraction chart of (Z)—N-[2-[3-chloro-5-(cyclopropylethynyl)pyridin-2-yl]-2-(isopropoximino)ethyl]-3-(difluoromethyl)-1-methyl-1H-pyrazole-4-carboxamide obtained in Example 12.

Powder X-ray diffraction of Compound (Z)-1 obtained in Example 12 was performed. The powder X-ray diffraction spectrum chart is shown in FIG. 4. In the powder X-ray diffraction spectrum chart, the following peak values were obtained as characteristic peaks. Peak values in the powder X-ray diffraction usually have a margin of error of ±0.2.
Diffraction angle (2θ): 7.54, 8.91, 9.67, 14.07, 14.50, 15.00, 15.88, 17.42, 17.95, 18.14, 20.74, 21.01, 21.77, 22.22, 22.54, 23.26, 25.49, 25.86 and 26.70.

Reference Example 12

Powder X-Ray Diffraction of Sulfate of Compound (Z)-1

Figure 5:
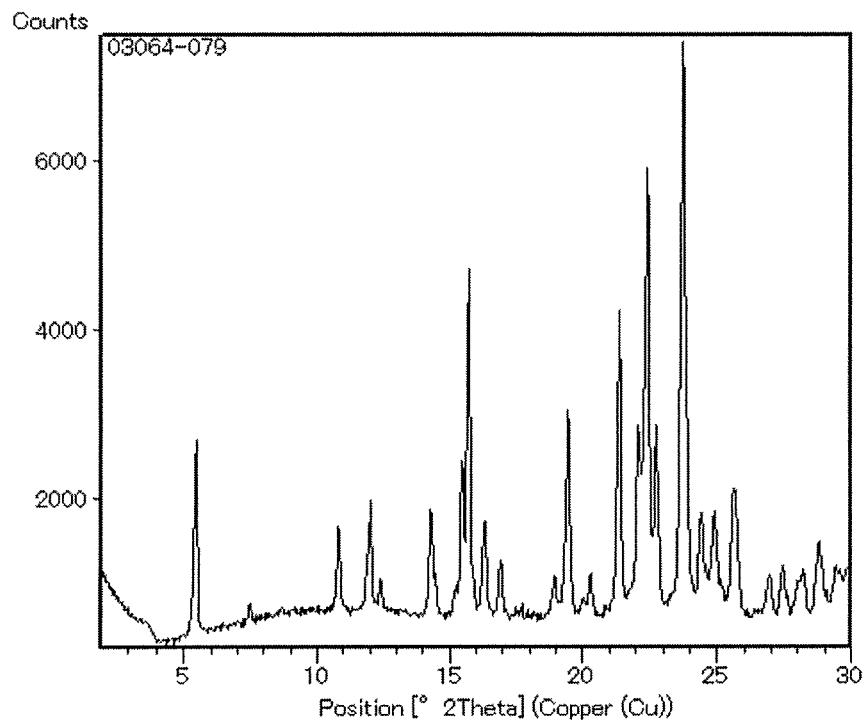
FIG. 5 A powder X-ray diffraction chart of (Z)—N-[2-[3-chloro-5-(cyclopropylethynyl)pyridin-2-yl]-2-(isopropoximino)ethyl]-3-(difluoromethyl)-1-methyl-1H-pyrazole-4-carboxamide sulfate obtained in Reference Example 4.

Powder X-ray diffraction of the sulfate of Compound (Z)-1 obtained in Reference Example 4 was performed. The powder X-ray diffraction spectrum chart is shown in FIG. 5. In the powder X-ray diffraction spectrum chart, the following peak values were obtained as characteristic peaks. Peak values in the powder X-ray diffraction usually have a margin of error of ±0.2.
Diffraction angle (2θ): 5.45, 10.81, 12.02, 14.29, 15.45, 15.70, 16.31, 19.44, 21.37, 22.07, 22.43, 22.75, 23.74, 24.41, 24.92 and 25.59.

Reference Example 13

Powder X-Ray Diffraction of Methanesulfonate of Compound (Z)-1

Figure 6:
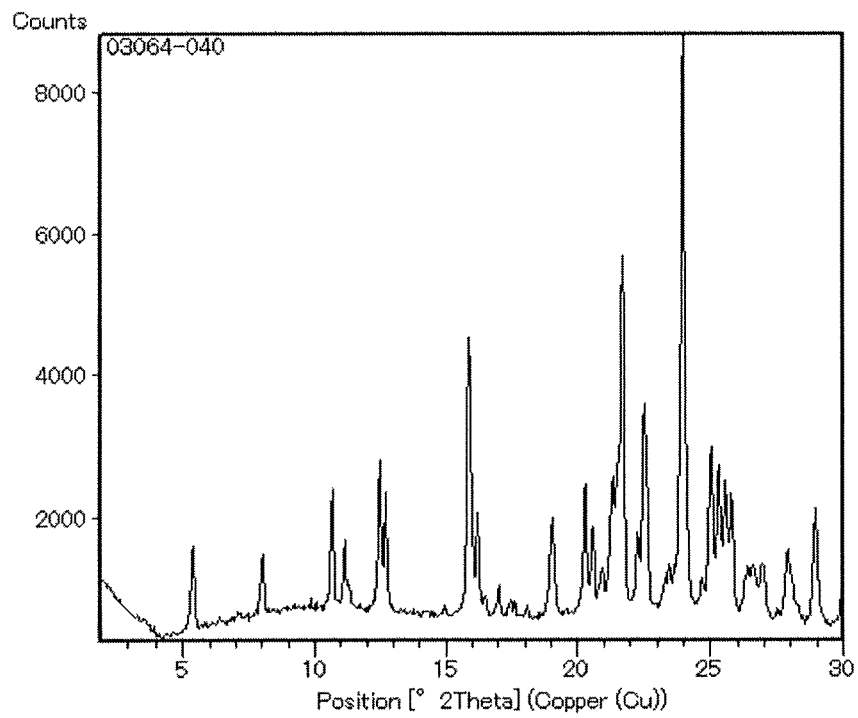
FIG. 6 A powder X-ray diffraction chart of (Z)—N-[2-[3-chloro-5-(cyclopropylethynyl)pyridin-2-yl]-2-(isopropoximino)ethyl]-3-(difluoromethyl)-1-methyl-1H-pyrazole-4-carboxamide methanesulfonate obtained in Reference Example 5.

Powder X-ray diffraction of the methanesulfonate of compound (Z)-1 obtained in Reference Example 5 was performed. The powder X-ray diffraction spectrum chart is shown in FIG. 6. In the powder X-ray diffraction spectrum chart, the following peak values were obtained as characteristic peaks. Peak values in the powder X-ray diffraction usually have a margin of error of ±0.2.
Diffraction angle (2θ): 5.39, 8.03, 10.68, 11.17, 12.50, 12.73, 15.86, 16.22, 19.07, 20.28, 20.57, 21.32, 21.72, 22.27, 22.53, 23.99, 25.03, 25.31, 25.56 and 25.79.

Reference Example 14

Powder X-Ray Diffraction of p-Toluenesulfonate of Compound (Z)-1

Figure 7:
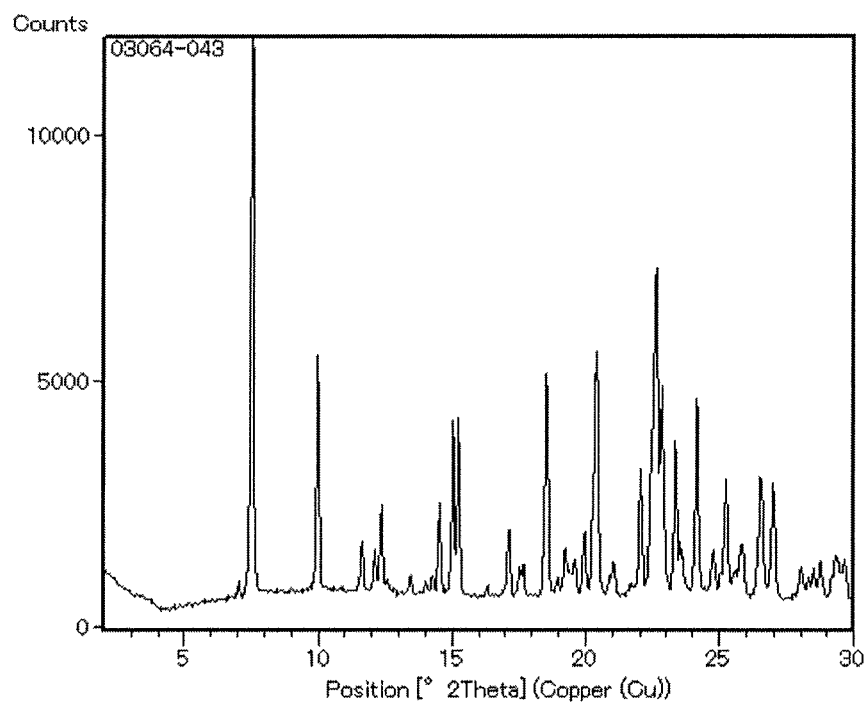
FIG. 7 A powder X-ray diffraction chart of (Z)—N-[2-[3-chloro-5-(cyclopropylethynyl)pyridin-2-yl]-2-(isopropoximino)ethyl]-3-(difluoromethyl)-1-methyl-1H-pyrazole-4-carboxamide p-toluenesulfonate obtained in Reference Example 6.

Powder X-ray diffraction of the p-toluenesulfonate of Compound (Z)-1 obtained in Reference Example 6 was performed. The powder X-ray diffraction spectrum chart is shown in FIG. 7. In the powder X-ray diffraction spectrum chart, the following peak values were obtained as characteristic peaks. Peak values in the powder X-ray diffraction usually have a margin of error of ±0.2.
Diffraction angle (2θ): 7.56, 9.99, 11.64, 12.37, 14.54, 15.04, 15.24, 17.14, 18.55, 19.97, 20.42, 22.04, 22.61, 22.84, 23.34, 24.15, 25.26, 26.52 and 26.97.

Reference Example 15

Powder X-Ray Diffraction of Oxalate of Compound (Z)-1

Figure 8:
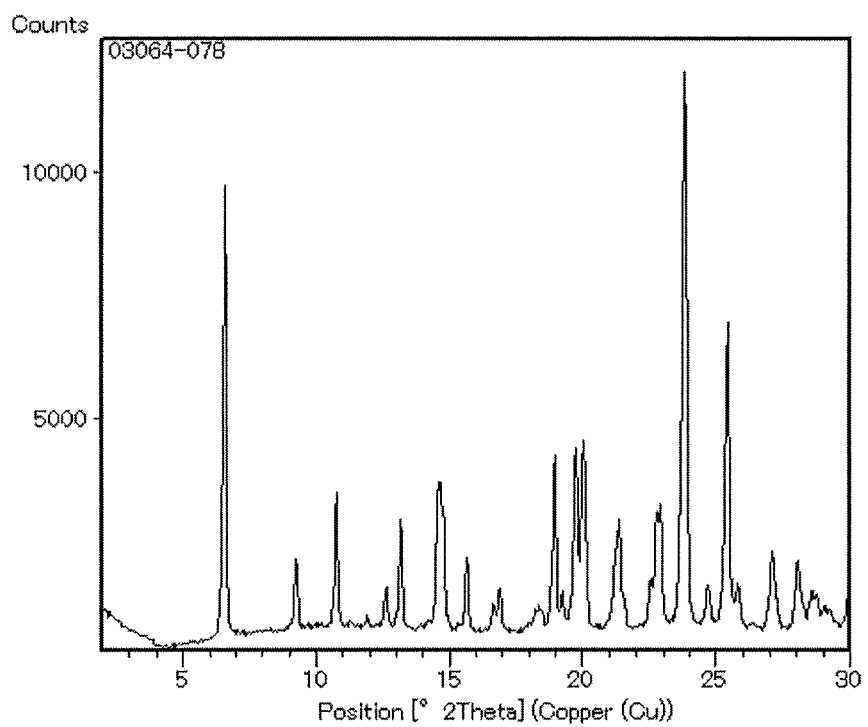
FIG. 8 A powder X-ray diffraction chart of (Z)—N-[2-[3-chloro-5-(cyclopropylethynyl)pyridin-2-yl]-2-(isopropoximino)ethyl]-3-(difluoromethyl)-1-methyl-1H-pyrazole-4-carboxamide oxalate obtained in Reference Example 7.

Powder X-ray diffraction of the oxalate of Compound (Z)-1 obtained in Reference Example 7 was performed. The powder X-ray diffraction spectrum chart is shown in FIG. 8. In the powder X-ray diffraction spectrum chart, the following peak values were obtained as characteristic peaks. Peak values in the powder X-ray diffraction usually have a margin of error of ±0.2.
Diffraction angle (2θ): 6.60, 9.26, 10.76, 13.17, 14.55, 14.78, 15.67, 18.97, 19.75, 20.02, 21.37, 22.92, 23.82, 25.45, 27.09 and 28.03.

Reference Example 16

Preparation of (Z)—N-[2-(3,5-dichloropyridin-2-yl)-2-(isopropoximino)ethyl]-3-(difluoromethyl)-1-methyl-1H-pyrazole-4-carboxamide

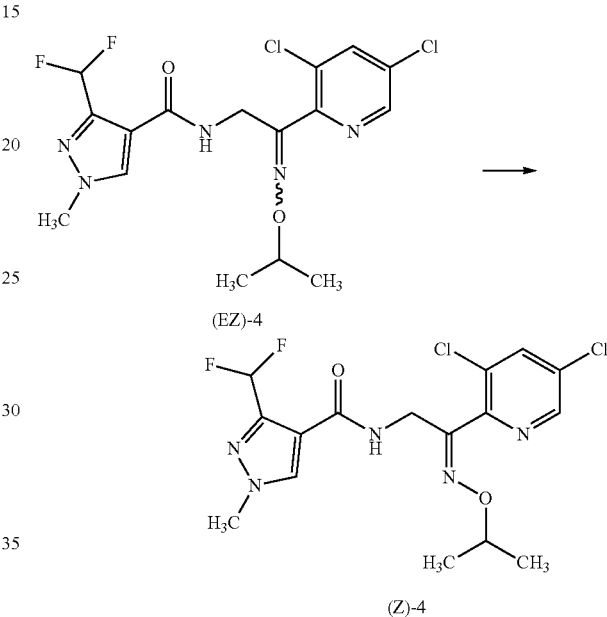

168 g of (EZ)—N-[2-(3,5-dichloropyridin-2-yl)-2-(isopropoximino)ethyl]-3-(difluoromethyl)-1-methyl-1H-pyrazole-4-carboxamide (Z-isomer/E-isomer=15.2/84.8) prepared in accordance with WO2014/010737 and 672 g of ethyl acetate were mixed at room temperature, and 20 mL of 4.5 mass % by weight hydrogen chloride/ethyl acetate (containing 0.056 equivalent of hydrogen chloride) was added to the resulting mixed solution at 35° C. The mixed solution was stirred at the same temperature for 1 hour, and then the solvent was distilled off under reduced pressure. Ethyl acetate was added to the resulting residue at room temperature to obtain 420 g of an ethyl acetate solution. 20 mL of 4.5 mass % hydrogen chloride/ethyl acetate (containing 0.056 equivalent of hydrogen chloride) was added to the ethyl acetate solution at 35° C. 252 g of n-heptane was added dropwise to the reaction solution at the same temperature over 1 hour, whereupon crystals precipitated. After the dropwise addition of n-heptane, the reaction mixture was stirred at the same temperature for 1 hour. After the stirring, 252 g of n-heptane was added dropwise over 1 hour, and the reaction mixture was stirred for 1 hour. After the stirring, 252 g of n-heptane was added dropwise over 1 hour, and the reaction mixture was stirred for 1 hour. The reaction mixture was then stirred at room temperature for 24 hours. The precipitated crystals were recovered by filtration and washed with a liquid mixture of 268.8 g of n-heptane and 67.2 g of ethyl acetate to give 144.5 g of the desired product as pale yellow crystals (yield 86.0%). According to qualitative analysis of the resulting crystals by HPLC, the area ratio of the peak for the Z-isomer to that for the E-isomer was 98.2/1.81.8, and the total area percentage of the two peaks was 98.6%.

m.p: 126.0 to 127.0° C.

$^1$H-NMR: δ8.61 (d, J=2.1 Hz, 1H), 8.55 (t, J=6.3 Hz, 1H), 8.25 (d, J=2.1 Hz, 1H), 8.14 (s, 1H), 7.15 (t, J=54.6 Hz, 1H), 4.35-4.20 (m, 3H), 3.89 (s, 3H), 1.10 (d, J=6.3 Hz, 6H).

INDUSTRIAL APPLICABILITY

The process for producing a geometrical isomer is quite useful as an effective process for producing an oximino compound useful as a medicine or an agrochemical.

The entire disclosure of Japanese Patent Application No. 2017-021298 filed on Feb. 8, 2017 and Japanese Patent Application No. 2017-241013 filed on Dec. 15, 2017 including specifications, claims, drawings and summaries are incorporated herein by reference in their entireties.

The invention claimed is:

1. A process for stereoselectively producing an oximino compound which produces the E-isomer of an oximino compound represented by the following formula (E)-1:

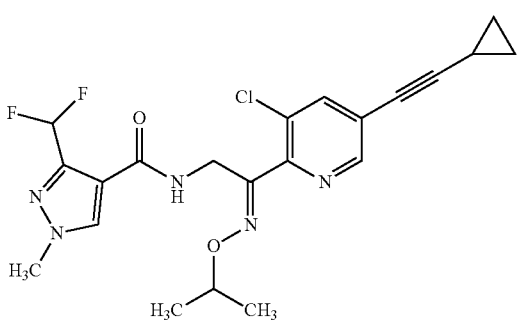

(E)-1 or the Z-isomer of an oximino compound represented by the following formula (Z)-1:

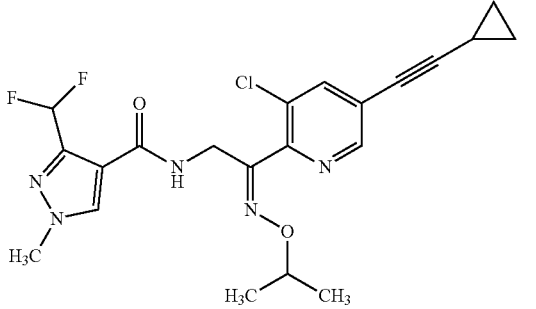

(Z)-1 from a mixture of geometrical isomers of an oximino compound represented by the following formula (EZ)-1:

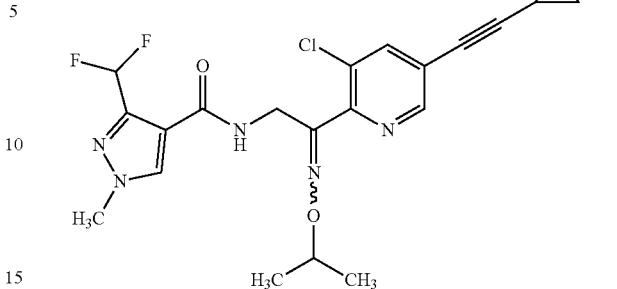

(EZ)-1 produces the Z-isomer of the oximino compound represented by the formula (Z)-1 from the E-isomer of the oximino compound represented by the formula (E)-1, or produces the E-isomer of the oximino compound represented by the formula (E)-1 from the Z-isomer of the oximino compound represented by the formula (Z)-1, the method comprising:

(i) mixing a mixture of the geometrical isomers represented by the formula (EZ)-1 or the Z-isomer of the oximino compound represented by the formula (Z)-1 as a starting material with at most 0.1 equivalent of an acidic compound, relative to the starting material, in a solvent to produce the E-isomer of the oximino compound represented by the formula (E)-1, or (ii) mixing a mixture of the geometrical isomers represented by the formula (EZ)-1 or the E-isomer of the oximino compound represented by the formula (E)-1 as a starting material with at least 0.7 equivalent of an acidic compound, relative to the starting material, in a solvent to produce the Z-isomer of the oximino compound represented by the formula (Z)-1.

2. The process for stereoselectively producing an oximino compound according to claim 1, wherein the starting material is a mixture of the geometrical isomers represented by the formula (EZ)-1.

3. The process for stereoselectively producing an oximino compound according to claim 1, wherein the acidic compound is added after the starting material is dissolved in the solvent.

4. The process for stereoselectively producing an oximino compound according to claim 1, which produces the E-isomer of the oximino compound represented by the formula (E)-1 by using at least 0.01 equivalent and at most 0.07 equivalent of the acidic compound, relative to the starting material.

5. The process for stereoselectively producing an oximino compound according to claim 1, which produces the Z-isomer of the oximino compound represented by the formula (Z)-1 by using at least 1.0 equivalent and at most 2.0 equivalent of the acidic compound, relative to the starting material.

6. The process for stereoselectively producing an oximino compound according to claim 1, wherein the acidic compound is a hydrogen halide, sulfuric acid or methanesulfonic acid.

7. The process for stereoselectively producing an oximino compound according to claim 1, wherein the solvent is at least one selected from the group consisting of aromatic hydrocarbon solvents, ether solvents, ketone solvents, ester solvents and halohydrocarbon solvents.

8. The process for stereoselectively producing an oximino compound according to claim 7, wherein the solvent is at least one selected from the group consisting of toluene, orthoxylene, cyclopentyl methyl ether, tertiary butyl methyl ether, dimethoxyethane, diethylene glycol dimethyl ether, methyl ethyl ketone, ethyl acetate and 1,2-dichloroethane.

9. The process for stereoselectively producing an oximino compound according to claim 1, which further comprises, after mixing the starting material and the acidic compound in the solvent, adding one or more solvents selected from aliphatic hydrocarbon solvents.

10. The process for stereoselectively producing an oximino compound according to claim 9, wherein the aliphatic hydrocarbon solvent is normal heptane.

11. The process for stereoselectively producing an oximino compound according to claim 1, wherein crystals, a salt or a solvate of the salt or a solvate is separated from the reaction system.

* * * * *